(12) United States Patent
Statsyuk et al.

(10) Patent No.: US 10,376,515 B2
(45) Date of Patent: Aug. 13, 2019

(54) ANALOGS OF ADENOSINE MONOPHOSPHATE (AMP) AS INHIBITORS OF UBIQUITIN-LIKE MODIFIER-ACTIVATING ENZYME ATG7

(71) Applicant: Northwestern University, Evanston, IL (US)

(72) Inventors: Alexander V. Statsyuk, Evanston, IL (US); Heeseon An, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 22 days.

(21) Appl. No.: 15/584,806

(22) Filed: May 2, 2017

(65) Prior Publication Data

US 2017/0312284 A1 Nov. 2, 2017

Related U.S. Application Data

(60) Provisional application No. 62/330,539, filed on May 2, 2016.

(51) Int. Cl.

| | | |
|---|---|---|
| *A01N 43/04* | (2006.01) | |
| *A61K 31/70* | (2006.01) | |
| *A61K 31/52* | (2006.01) | |
| *A61K 31/131* | (2006.01) | |
| *A61K 31/133* | (2006.01) | |
| *A61K 31/135* | (2006.01) | |
| *A61K 31/695* | (2006.01) | |
| *A61K 31/365* | (2006.01) | |
| *A61K 45/00* | (2006.01) | |
| *C07D 471/04* | (2006.01) | |
| *C07H 19/14* | (2006.01) | |
| *A61K 31/708* | (2006.01) | |
| *A61K 31/7076* | (2006.01) | |
| *C07H 19/23* | (2006.01) | |
| *C07H 19/22* | (2006.01) | |

(52) U.S. Cl.
CPC ............ *A61K 31/52* (2013.01); *A61K 31/131* (2013.01); *A61K 31/133* (2013.01); *A61K 31/135* (2013.01); *A61K 31/365* (2013.01); *A61K 31/695* (2013.01); *A61K 45/05* (2013.01); *C07D 471/04* (2013.01); *A61K 31/708* (2013.01); *A61K 31/7076* (2013.01); *C07H 19/14* (2013.01); *C07H 19/22* (2013.01); *C07H 19/23* (2013.01)

(58) Field of Classification Search
None
See application file for complete search history.

(56) References Cited

PUBLICATIONS

Aronov et al. Bioorganic & Medicinal Chemistry Letters (1998), vol. 8, pp. 3505-3510.*
Herforth et al. J. Comb. Chem. (2002), vol. 4, pp. 302-314.*
An et al. JACS (2013), vol. 135, pp. 16948-16962.*
Dou, Z.; Xu, C.; Donahue, G.; Shimi, T.; Pan, J. A.; Zhu, J.; Ivanov, A.; Capell, B. C.; Drake, A. M.; Shah, P. P.; Catanzaro, J. M.; Daniel Ricketts, M.; Lamark, T.; Adam, S. A.; Marmorstein, R.; Zong, W. X.; Johansen, T.; Goldman, R. D.; Adams, P. D.; Berger, S. L. Nature 2015, 527, 105.
Guo, J. Y.; Karsli-Uzunbas, G.; Mathew, R.; Aisner, S. C.; Kamphorst, J. J.; Strohecker, A. M.; Chen, G.; Price, S.; Lu, W.; Teng, X.; Snyder, E; Santanam, U.; Dipaola, R. S.; Jacks, T.; Rabinowitz, J. D.; White, E. Genes & development 2013, 27, 1447.
Karsli-Uzunbas, G.; Guo, J. Y.; Price, S.; Teng, X.; Laddha, S. V.; Khor, S.; Kalaany, N. Y.; Jacks, T.; Chan, C. S.; Rabinowitz, J. D.; White, E Cancer discovery 2014, 4, 914.
Mizushima, N.; Komatsu, M. Cell 2011, 147, 728.
Rosenfeldt, M. T.; O'Prey, J.; Morton, J. P.; Nixon, C.; MacKay, G.; Mrowinska, A.; Au, A.; Rai, T. S.; Zheng, L; Ridgway, R.; Adams, P. D.; Anderson, K. I.; Gottlieb, E.; Sansom, O. J.; Ryan, K. M. Nature 2013, 504, 296.
Wu, Y. T.; Tan, H. L; Shui, G.; Bauvy, C.; Huang, Q.; Wenk, M. R.; Ong, C. N.; Codogno, P.; Shen, H. M. The Journal of biological chemistry 2010, 285, 10850.

* cited by examiner

*Primary Examiner* — Patrick T Lewis
(74) *Attorney, Agent, or Firm* — Quarles & Brady LLP

(57) ABSTRACT

Disclosed are analogs of adenosine monophosphate (AMP) as inhibitors of ubiquitin-like modifier-activing enzyme ATG7. The AMP analogs may be formulated as pharmaceutical compositions for treating diseases or disorders that depend on ATG7 activity and/or autophagy such as cell proliferative diseases and disorders.

14 Claims, 7 Drawing Sheets

ANALOGS OF ADENOSINE MONOPHOSPHATE (AMP) AS INHIBITORS OF UBIQUITIN-LIKE MODIFIER-ACTIVATING ENZYME ATG7

CROSS-REFERENCE TO RELATED PATENT APPLICATIONS

The present application claims the benefit of priority under 35 U.S.C. § 119(e) to U.S. Provisional Application No. 62/330,539, filed on May 2, 2016, the content of which is incorporated herein by reference in its entirety.

BACKGROUND

The field of the invention relates to small molecular inhibitors of enzymes involved in autophagy. In particular, the field of the invention relates to small molecular inhibitors of ubiquitin-like modifier-activating enzyme ATG7 which are analogs of adenosine monophosphate (AMP).

Rapidly proliferating cancer cells need free amino acid building blocks to meet their metabolic needs and to maintain proper organelle quality control. Autophagy or the process of "self eating" plays an essential role to supply the intracellular pool of amino acids by degrading intracellular organelles/proteins as well as proteins scavenged from the extracellular space. Therefore, inhibition of autophagy is promising strategy to treat cancers, because autophagy inhibitors will reduce the internal supply of free amino acids for cancer cells, resulting in the inhibition of cancer cell growth.

In addition, autophagy inhibitors can lead to accumulation of defective mitochondria leading to the increase in reactive oxygen species in cancer cells, which leads to inhibition of cell proliferation, and conversion of malignant cancer cells into benign tumors called oncocytomas. This conversion to oncocytomas occurs because defective mitochondria are removed via the autophagy pathway, and if autophagy is inhibited then defective mitochondria accumulate. In addition, in some types of cancers autophagy is involved in clearing misfolded proteins to alleviate endoplasmic reticulum (ER) stress. In such cases inhibition of autophagy leads to accumulation of misfolded proteins in the ER, ER stress and apoptosis. In recent years, emerging evidence shows that autophagy is particularly important for the survival of K-Ras driven pancreatic and lung cancers, and B-Raf (V600E) driven melanomas and lung cancers, as well as PTEN deficient prostate cancers. This opens the path for using autophagy inhibitors in personalized therapy; i.e. for example if the tumor in patient is driven by K-Ras or B-Raf V600E mutation or PTEN deficiency than a decision could be made to administer autophagy inhibitors as therapeutics for such tumors (see: *Genes & Dev.* 2016. 30: 399-407; *Cancer Discov.* 2015 April; 5(4):410-23; *Genes & Dev.* 2013. 27: 1447-1461; *Cancer Discov.* 2013 November; 3(11):1272-85; *Nature,* 2015, 524, 361-365).

In particular, ubiquitin-like modifier-activating enzyme ATG7 presents a potential target for autophagy inhibitors. Ubiquitin-like modifier-activating enzyme ATG7 is an essential enzyme which is important for autophagy activation, and inhibition of ATG7 using gene knock-out techniques in vivo has been shown to inhibit the growth of K-Ras driven pancreatic and lung cancers, V600E B-Raf melanoma and lung cancers, and PTEN deficient prostate cancers (*Genes & Dev.* 2016. 30: 399-407; *Cancer Discov.* 2015 April; 5(4): 410-23; *Cancer Discov.* 2013 November; 3(11):1272-85; *Nature,* 2015, 524, 361-365; Nature. 2013 Dec. 12; 504 (7479):296-300; Autophagy. 2014 February; 10(2):384-5; Genes Dev. 2013 Jul. 1; 27(13):1447-61). Therefore, ATG7 is a potential drug target to treat these devastating diseases. In the present disclosure, we propose the development of first in class ATG7 covalent inhibitors using a novel inhibitor design concept that exploits the conformational flexibility of ATG7 enzyme in binding to adenosine monophosphate (AMP). The disclosed AMP analog inhibitors of ATG7 have the potential to become anticancer drugs.

SUMMARY

Disclosed are novel compounds which may function as AMP analogs. The compounds may be used to inhibit ubiquitin-like modifier-activating enzyme ATG7, which is involved in the process of autophagy. As such, the disclosed compounds may be used to inhibit autophagy and treat diseases and disorders that depend on autophagy.

The disclosed compounds may function as analogs of AMP. The disclosed compounds may have a Formula I:

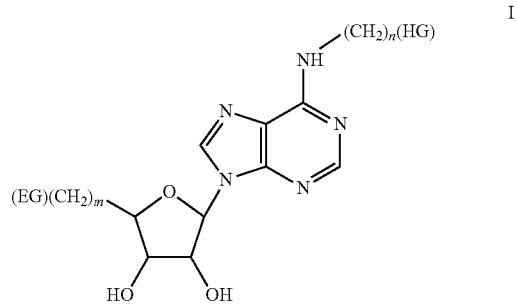

where m is an integer selected from 0-6; EG is an electrophilic group; n is an integer selected from 0-6; and HG is a hydrophobic group and optionally a group containing only carbon atoms and/or hydrogen atoms.

In some embodiments of the disclosed compounds, HG is phenyl or benzyl optionally substituted at one or more positions with $C_1$-$C_6$-alkynyl, $C_1$-$C_6$-alkenyl, or $C_1$-$C_6$-alkyl, or halo (in particular F, Cl, or Br); HG is $C_1$-$C_6$-alkynyl, $C_1$-$C_6$-alkenyl, $C_1$-$C_6$-alkyl, which may be straight chain or branched and optionally substituted at one or more positions with a heteroatom (e.g., N, O, S, P, Se, and B); or HG is a $C_3$-$C_7$ homocycle or heterocycle (e.g., containing one or more heteroatoms selected from N, O, S, P, Se, and B), optionally saturated or unsaturated at one or more bonds and optionally substituted at one or more positions with a hydrophobic group (e.g., hydrophobic substituents such as $C_1$-$C_6$-alkyl, $C_1$-$C_6$-alkenyl, $C_1$-$C_6$-alkynyl, or halo), such as cyclohexyl, phenyl, pyrazol, pyridinyl, or pyrazinyl optionally substituted at one or more positions with $C_1$-$C_6$-alkynyl, $C_1$-$C_6$-alkenyl, $C_1$-$C_6$-alkyl, or halo.

In some embodiments of the disclosed compounds, EG is not hydroxymethyl. In other embodiments of the disclosed compounds, EG is not $NH_2SO_2O$— or $NH_2SO_2OCH_2$—.

In some embodiments of the disclosed compounds, EG may have a formula: Y—X— or Y—X—$CH_2$—, where the compounds have a Formula Ia:

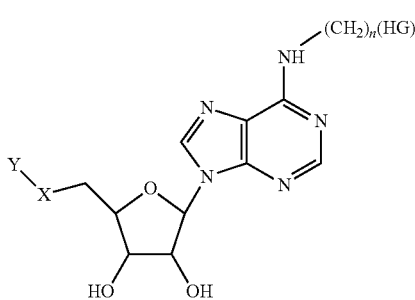

Ia where X is C, N, O, or S; Y comprises an electrophile; n is an integer selected from 0-6; and HG is a hydrophobic group as defined for Formula I above. In some embodiments of the compounds of Formula Ia, X is not O and rather is N or S. In some embodiments of the compounds having a formula Ia, Y may have a formula $CH_2CHSO_2$—, which includes a vinyl group that may function as an electrophile.

Preferably, the disclosed compounds bind to ATG7 and inhibit the activity of ATG7. Even more preferably, the disclosed compounds inhibit the activity of ATG7 irreversibly. The disclosed compound may inhibit the activity of ATG7 via binding to the AMP binding pocket of ATG7 and forming a covalent bond between the electrophile of the disclosed compounds and the sulfur atom of the catalytic cysteine of ATG7.

Also disclosed are pharmaceutical compositions that comprise the disclosed compounds together with a carrier, diluent, or excipient. The pharmaceutical compositions may comprise an effective amount of the compounds (or salts, esters, amides, or solvates thereof) for treating and/or preventing a disease, disorder, or condition which may include cell proliferation diseases, disorders, or conditions, such as cancer.

Also disclosed are methods of treating cancer that include administering the disclosed compounds, for example, where the compounds are formulated as a pharmaceutical composition and administered to a subject having cancer or suspected of having cancer. Cancers treated by the disclosed methods may include, but are not limited to lung cancer, melanoma, pancreatic cancer, colon cancer, cancer of the central nervous system, ovarian cancer, renal cancer, prostate cancer, breast cancer, multiple myeloma, leukemia, and any other cancer whose proliferation depends on autophagy.

DETAILED DESCRIPTION

Figure 1:
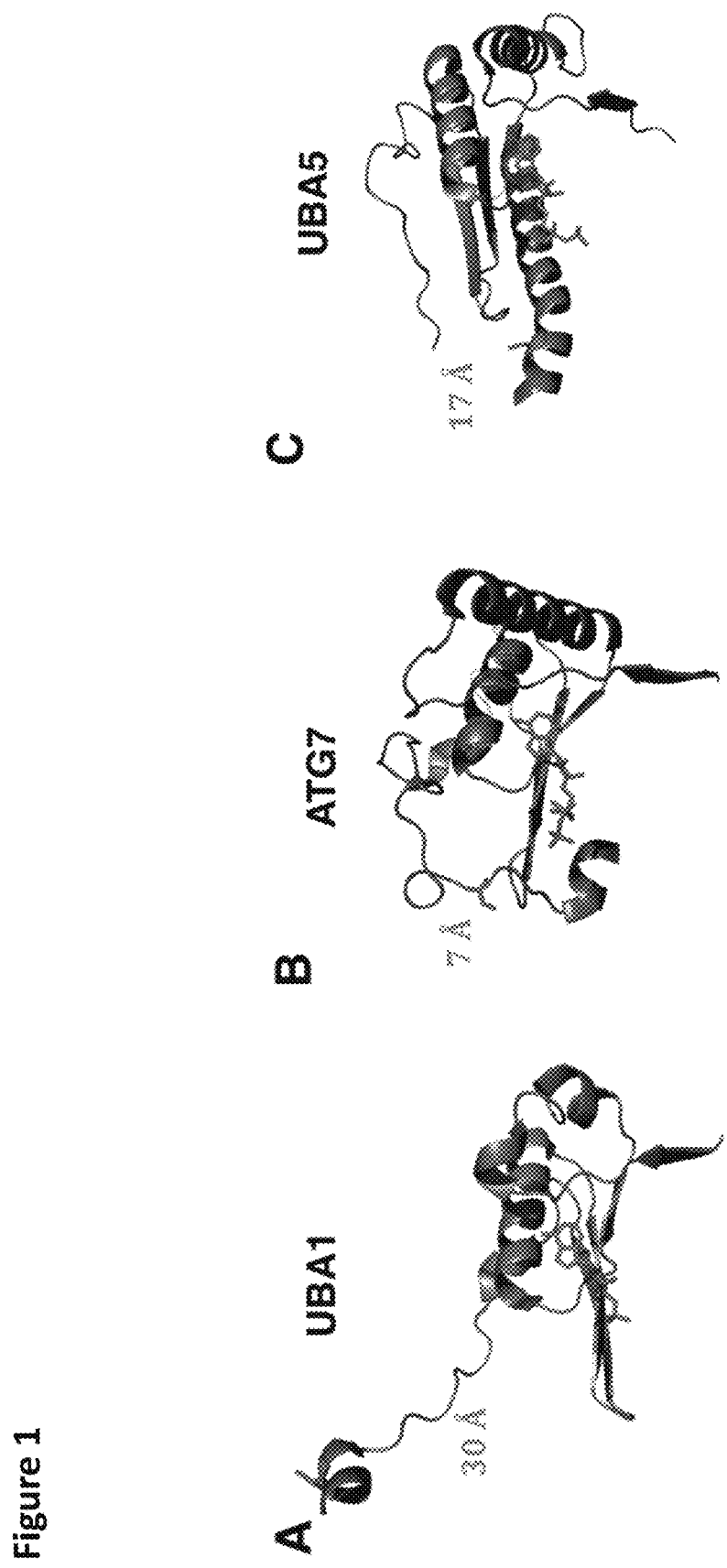
FIG. 1. Representative crystal structures of canonical and non-canonical E1s (A) Canonical UBA1 shows >30 Å distance between the catalytic cysteine and ATP binding center (B) The catalytic cysteine of non-canonical ATG7 is ~7 Å away from the ATP binding center (C) The catalytic cysteine of noncanonical UBA5 is positioned 17 Å from the ATP binding center.

Disclosed herein are compounds which may function as adenosine monophosphate (AMP) analogs and may be used for treatment of cancer and other proliferative disorders. The present invention is described herein using several definitions, as set forth below and throughout the application.

Unless otherwise specified or indicated by context, the terms "a", "an", and "the" mean "one or more." For example, "a compound" should be interpreted to mean "one or more compounds."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a plus sign "+" as part of a molecular formula for a radical group or substituent group may be used to designate the point of attachment and bonding for the radical group or the substituent group.

The term "alkyl" as contemplated herein includes a straight-chain or branched alkyl radical in all of its isomeric forms. In some embodiments, alkyl groups may include 1-12 carbon atoms.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with an inhibitor of autophagy, including a disease, disorder, or condition that is responsive to therapy with an inhibitor of ubiquitin-like modifier-acting enzyme ATG7. For example, a "subject in need of treatment" may include a subject having a cell proliferative disease, disorder, or condition such as cancer, including cancers such as lung cancer (e.g., non-small cell lung cancer and/or K-Ras driven lung cancer), melanoma (e.g., V600E B-Raf melanoma), pancreatic cancer (e.g., K-Ras driven pancreatic cancers), colon cancer, cancer of the central nervous system, ovarian cancer, renal cancer, prostate cancer, breast cancer, multiple myeloma, leukemia, and any other cancer whose proliferation depends on autophagy.

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

The formulae of the compounds disclosed herein should be interpreted as encompassing all possible stereoisomers, enantiomers, or epimers of the compounds unless the formulae indicates a specific stereoisomer, enantiomer, or epimer. The formulae of the compounds disclosed herein should be interpreted as encompassing salts, esters, amides, or solvates thereof of the compounds. Pro-drugs of the disclosed compounds are contemplated. For example, pro-drugs of the disclosed compounds may be formed by reacting the electrophile group of the disclosed compounds with a glutathione or another type of thiol to form a pro-drug conjugate. The pro-drug conjugate may be administered to a subject in need thereof and may decompose via reversible reaction into the original compound with the electrophile group and the corresponding glutathione or other thiol. The resulting electrophile group of the decomposed pro-drug conjugate can then react with ATG7 and cause the desired pharmacological effects.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a subject (e.g., after about 1, 2, 3, 4, 5, or 6 hours post-administration), the concentration of the compound at the site of action is about 2 to 10 μM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Adenosine Monophosphate (AMP) Analogs for Inhibiting Ubiquitin-Like Modifier-Activing Enzyme ATG7

Disclosed are novel compounds that may function as AMP analogs. The disclosed compounds may be used to inhibit ubiquitin-like modifier-activing enzyme ATG7, which is involved in the process of autophagy. As such, the disclosed compounds may be used to inhibit autophagy and treat diseases and disorders that depend on autophagy.

The disclosed compounds typically have a Formula I:

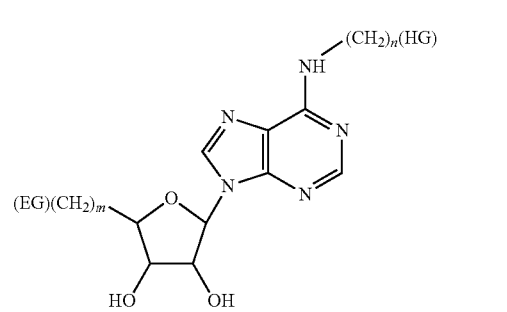

where m is an integer selected from 0-6; EG is an electrophilic group; n is an integer selected from 0-6; and HG is a hydrophobic group.

In some embodiments of the disclosed compounds, HG is phenyl or benzyl optionally substituted at one or more positions with $C_1$-$C_6$-alkynyl, $C_1$-$C_6$-alkenyl, $C_1$-$C_6$-alkyl, or halo (in particular F, Cl, or Br). In other embodiments, HG is $C_1$-$C_6$-alkynyl, $C_1$-$C_6$-alkenyl, $C_1$-$C_6$-alkyl, which may be straight chain or branched and optionally substituted with heteroatoms such as N, O, S, P, Se, and B. In even further embodiments, HG is a $C_3$-$C_7$ homocycle or heterocycle (optionally substituted with a heteroatom such as N, O, S, P, Se, and B), optionally saturated or unsaturated at one or more bonds and optionally substituted at one or more positions with a hydrophobic group (e.g., hydrophobic substituents such as alkyl, alkenyl, alkynyl, or halo). HG may be a saturated homocycle, such as cyclohexyl, or HG may be a saturated heterocycle, such as piperidinyl, which optionally substituted at one or more positions with $C_1$-$C_6$-alkynyl, $C_1$-$C_6$-alkenyl, $C_1$-$C_6$-alkyl, or halo. HG may be an unsaturated homocycle, such as phenyl, and/or HG may be an unsaturated heterocycle, such as pyrazol, pyridinyl, or pyrazinyl, optionally substituted at one or more positions with $C_1$-$C_6$-alkynyl, $C_1$-$C_6$-alkenyl, $C_1$-$C_6$-alkyl, or halo. In some embodiments, HG comprises only carbon atoms and/or hydrogen atoms.

In some embodiments of the disclosed compounds, EG may have a formula selected from the following group of formulas, where $R_1$ represents the adenosine riboside moiety of the compound:

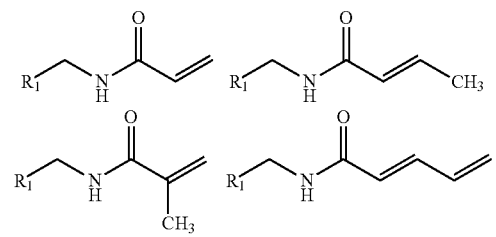

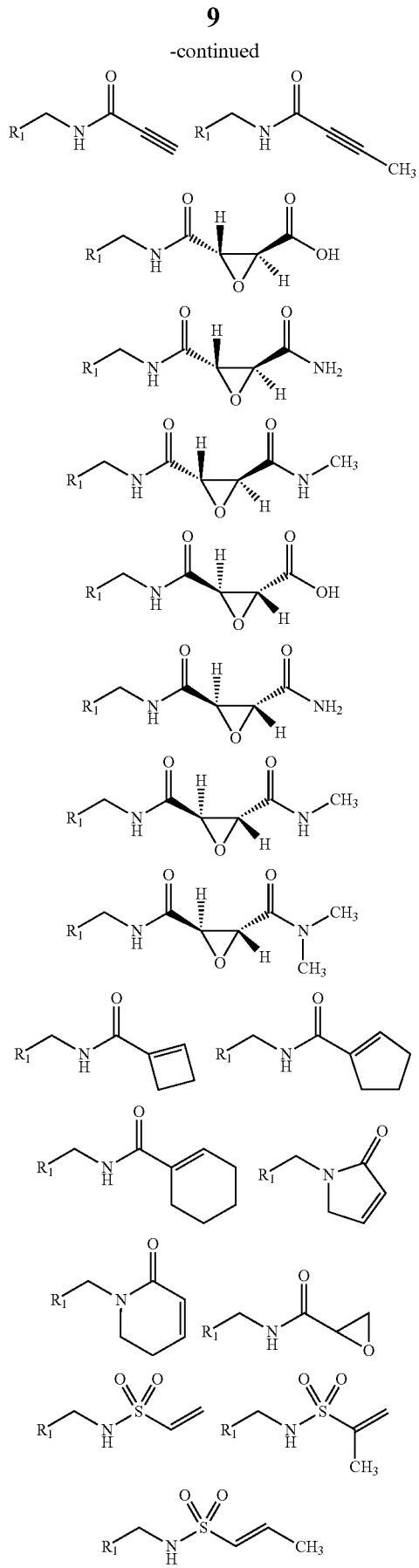

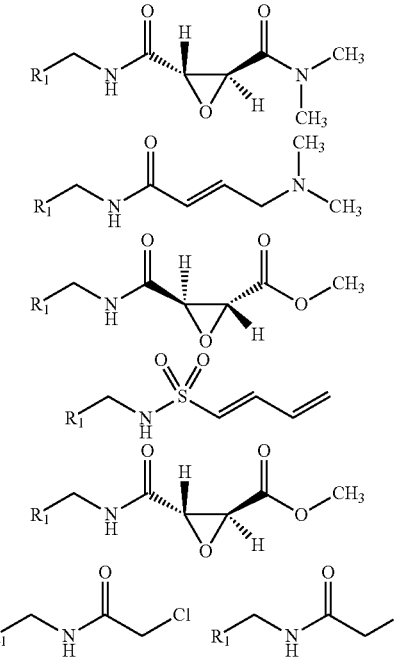

In some embodiments of the disclosed compounds, optionally EG is not hydroxymethyl. In other embodiments of the disclosed compounds, optionally EG is not $NH_2SO_2O-$ or $NH_2SO_2OCH_2-$.

In some embodiments of the disclosed compounds, EG may have a formula: Y—X— or Y—X—$CH_2$—, where the compounds have a Formula Ia:

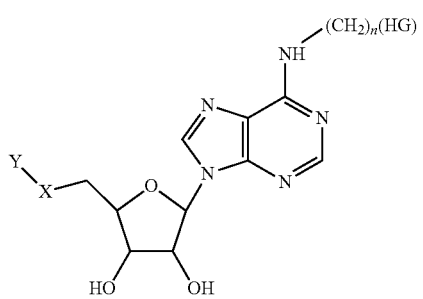

where X is C, N, O, or S; Y comprises an electrophile; n is an integer selected from 0-6; and HG is a hydrophobic group as defined for Formula I above. In some embodiments of the compounds of Formula Ia, X is not O.

In the compounds having a Formula Ia, Y comprises an electrophile. In particular, Y may have a formula $CH_2CHSO_2-$, which includes a vinyl group that may function as an electrophile. In further embodiments of compounds having Formula Ia, Y may be an electrophile selected from the group consisting of:

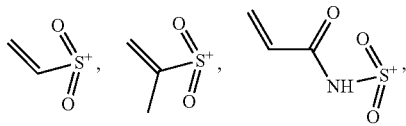

-continued

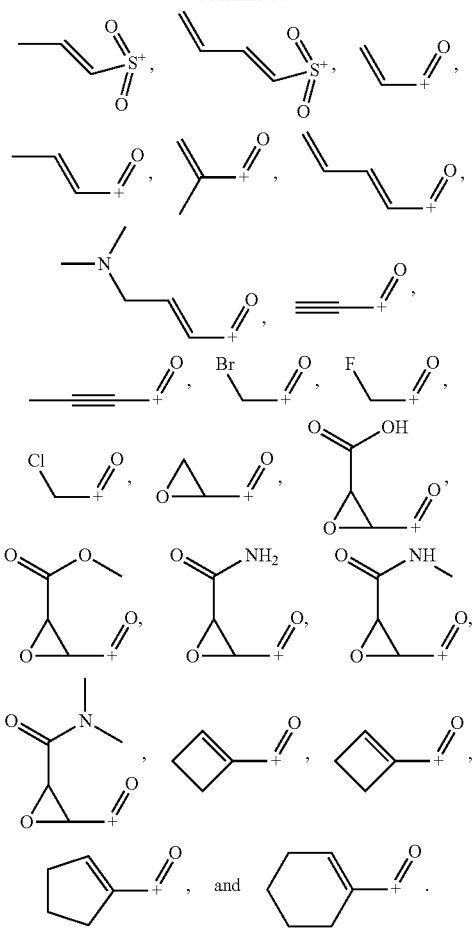

In some embodiments of the disclosed compounds, the compounds may have a Formula Ia':

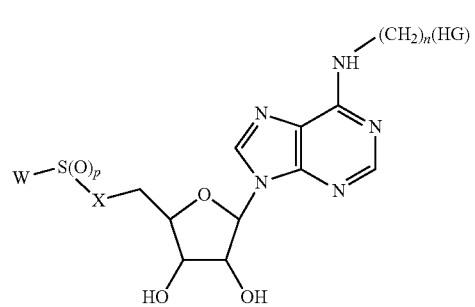

where X is C, N, or O; p is an integer selected from 0-2; W comprises an electrophile; n is an integer selected from 0-6, and HG is a hydrophobic group as defined for Formula I above. In some embodiments of the compounds having a Formula Ia', W is selected from:

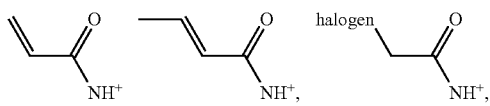

-continued

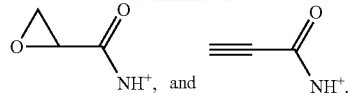

In some embodiments of Formula Ia, Y and X may form a homocycle or a heterocycle, such as a 3-membered, 4-membered, 5-membered, 6-membered, or 7-membered homocycle or heterocycle which optionally is unsaturated at one or more bonds, and which optionally includes a carbonyl substitution. Suitable homocycles or heterocycles may include, but are not limited to

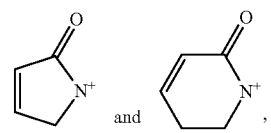

where the compounds have a formula:

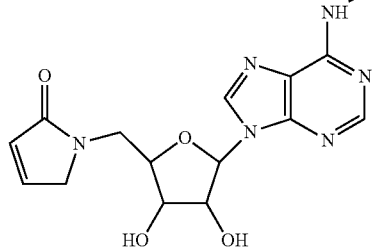

In some embodiments, the disclosed compounds may have a Formula Ib:

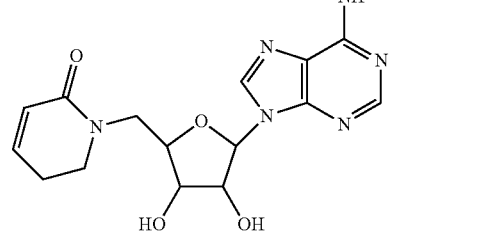

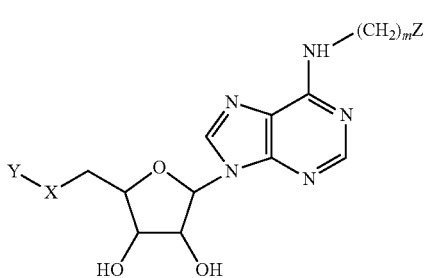

where X and Y are as described for Formula Ia or elsewhere herein; m is an integer selected from 0-6; and Z is a $C_3$-$C_7$ homocycle or heterocycle, optionally saturated or unsaturated at one or more bonds and optionally substituted at one or more positions with a hydrophobic group (e.g., hydrophobic substituents such as $C_1$-$C_6$-alkynyl, $C_1$-$C_6$-alkenyl, or $C_1$-$C_6$-alkyl). Optionally, Z may include only carbon atoms and/or hydrogen atoms. In some specific embodiments, Y may be optionally substituted phenyl, and the disclosed compounds may have a Formula Ib'

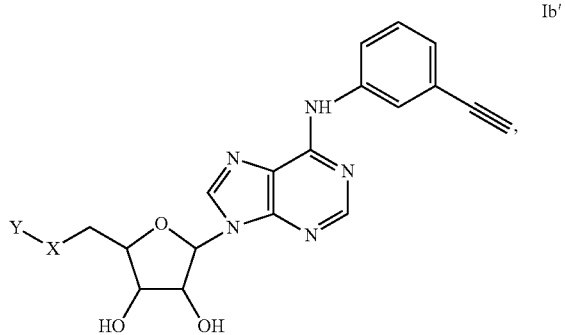

where X and Y are as described for Formula Ia or elsewhere herein.

In other embodiments, Y may be $C_1$-$C_6$-alkynyl and the disclosed compounds may have a Formula Ic:

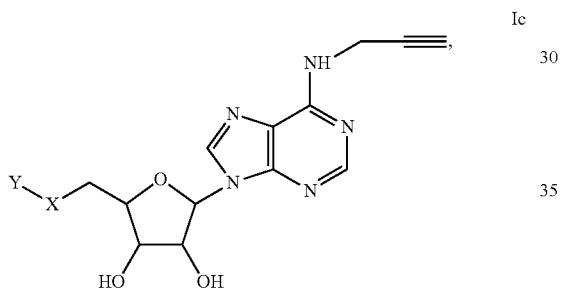

where X and Y are as described for Formula Ia or elsewhere herein.

Preferably, the disclosed compounds bind to ATG7 (preferably with a $K_d$ of less than about 1, 0.5, 0.1, 0.05, 0.01, 0.005, or 0.001 μm) and inhibit the activity of ATG7. Even more preferably, the disclosed compounds inhibit the activity of ATG7 irreversibly. The disclosed compound may inhibit the activity of ATG7 via binding to the AMP binding pocket of ATG7 and forming a covalent bond between the electrophile of the disclosed compounds and the sulfur atom of the catalytic cysteine of ATG7.

Also disclosed herein are pharmaceutical compositions. The disclosed pharmaceutical compositions comprise an effective amount of any of the compounds disclosed herein together with a carrier, excipient, or diluent.

Also disclosed herein are methods for treating a subject in need thereof comprising administering the any of the compounds disclosed or administering any of the pharmaceutical compositions comprising any of the compounds disclosed herein. In the disclosed methods, the subject may have a disease or disorder that is treated by inhibiting ubiquitin-like modifier-activating enzyme ATG7, optionally wherein the disease or disorder is cancer. Cancers treated by the disclosed methods may include, but are not limited to lung cancer (e.g., non-small cell lung cancer and/or K-Ras driven lung cancer), melanoma (e.g., V600E B-Raf melanoma), pancreatic cancer (e.g., K-Ras driven pancreatic cancers), colon cancer, cancer of the central nervous system, ovarian cancer, renal cancer, prostate cancer, breast cancer, multiple myeloma, leukemia, and any other cancer whose proliferation depends on autophagy.

The AMP analogs disclosed herein may be synthesized using methods disclosed in the art, for example, An, H.; Statsyuk, A. V., "Development of an Activity-Based Probe for Ubiquitin and Ubiquitin Protein Activating Enzymes," J. Am. Chem. Soc., 2013, 135(45), 16948-16962, the content of which is incorporated herein by reference in its entirety. AMP analogs and methods of synthesizing AMP analogs also are disclosed in An, H.; Statsyuk, A. V., "An Inhibitor of Ubiquitin Conjugation and Aggresome Function," Chem. Sci. 2015, 6, 5235-5245, the content of which is incorporated herein by reference in its entirety. Finally, AMP analogs, probes, and methods of synthesizing AMP analogs also are disclosed in An, H.; Statsyuk, A. V., "Facile synthesis of covalent probes to capture enzymatic intermediates during E1 enzyme catalysis," Chem. Commun., 2016, 52, 2477-2480, the content of which is incorporated herein by reference in its entirety.

ILLUSTRATIVE EMBODIMENTS

The following embodiments are illustrative and are not intended to limit the scope of the claimed subject matter.

Embodiment 1

A compound having a Formula I:

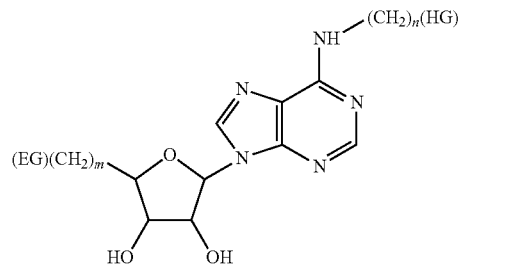

wherein: EG is an electrophilic group; m is an integer selected from 0-6; n is an integer selected from 0-6; and HG is a hydrophobic group.

Embodiment 2

The compound of embodiment 1 having a Formula IA:

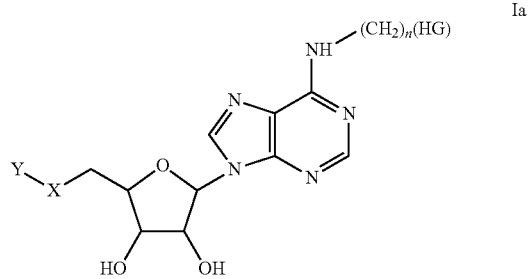

wherein: X is C, N, O, or S; Y is an electrophile; n is an integer selected from 0-6; and HG is a hydrophobic group.

Embodiment 3

The compound of embodiment 1 or 2, wherein Y is selected from the group consisting of:

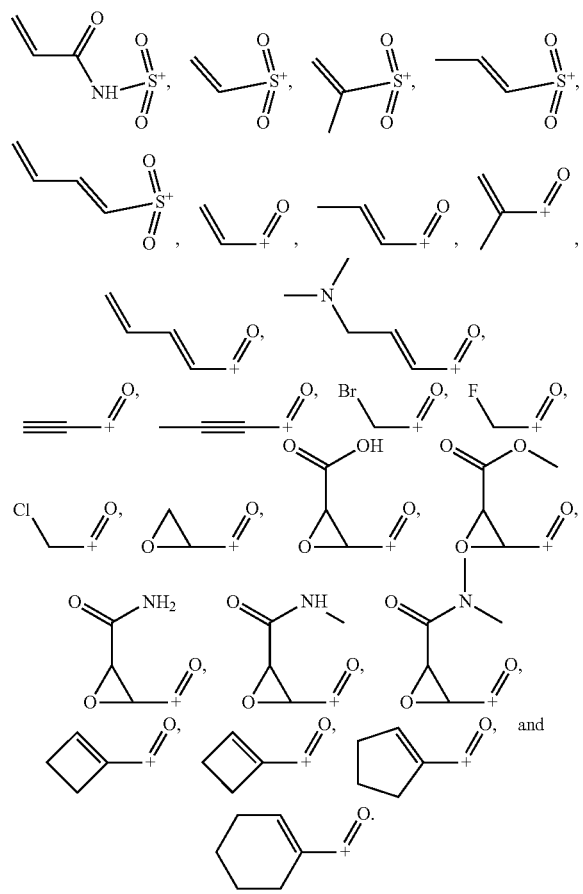

Embodiment 4

The compound of embodiment 2, wherein Y and X form a 3-membered, 4-membered, 5-membered, 6-membered, or 7-membered homocycle or heterocycle which optionally is unsaturated at one or more bonds and which optionally includes a carbonyl substituent.

Embodiment 5

The compound of embodiment 4, wherein Y and X form an unsaturated heterocycle selected from

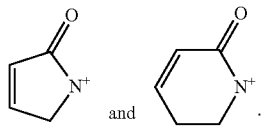 [SMILES: O=C1C=CC[NH2+]1 ; O=C1C=CCC[NH2+]1]

Embodiment 6

The compound of any of embodiments 2-5, wherein X is O or S.

Embodiment 7

The compound of any of embodiments 2-5, wherein X is N.

Embodiment 8

The compound of any of embodiments 2-5, wherein X is C.

Embodiment 9

The compound of any of the foregoing embodiments, wherein HG is phenyl or benzyl optionally substituted at one or more positions with $C_1$-$C_6$-alkynyl; HG is $C_1$-$C_6$-alkynyl, alkenyl, alkyl, cycloalkyl, or halo (F, Cl, or Br in particular); or HG is a $C_3$-$C_7$ homocycle or heterocycle, optionally unsaturated at one or more positions with a hydrophobic substituent (e.g., $C_1$-$C_6$-alkyl, $C_1$-$C_6$-alkenyl, $C_1$-$C_6$-alkynyl, or halo), such as cyclohexyl, phenyl, pyrazol, pyridinyl, or pyrazinyl, optionally substituted at one or more positions with $C_1$-$C_6$-alkyl, $C_1$-$C_6$-alkenyl, $C_1$-$C_6$-alkynyl, or halo.

Embodiment 10

The compound of any of the foregoing embodiments, wherein EG comprises a vinyl group=+.

Embodiment 11

The compound of any of the foregoing embodiments having a Formula Ib:

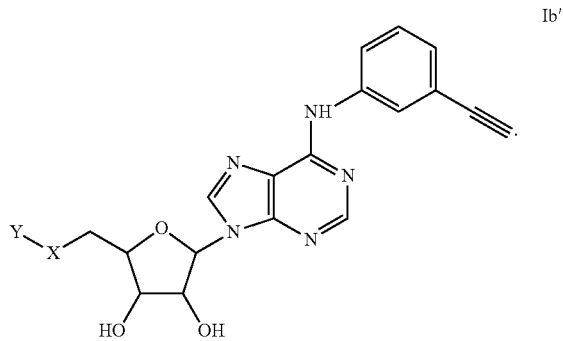

Embodiment 12

The compound of any of the foregoing embodiments having a Formula Ic.

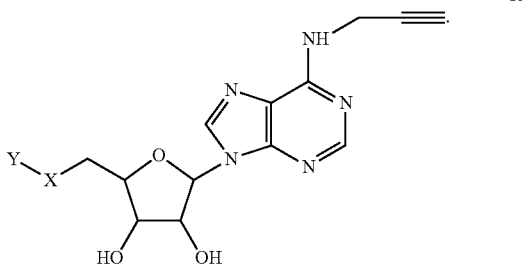

Embodiment 13

The compound of any of the foregoing embodiments having a formula selected from

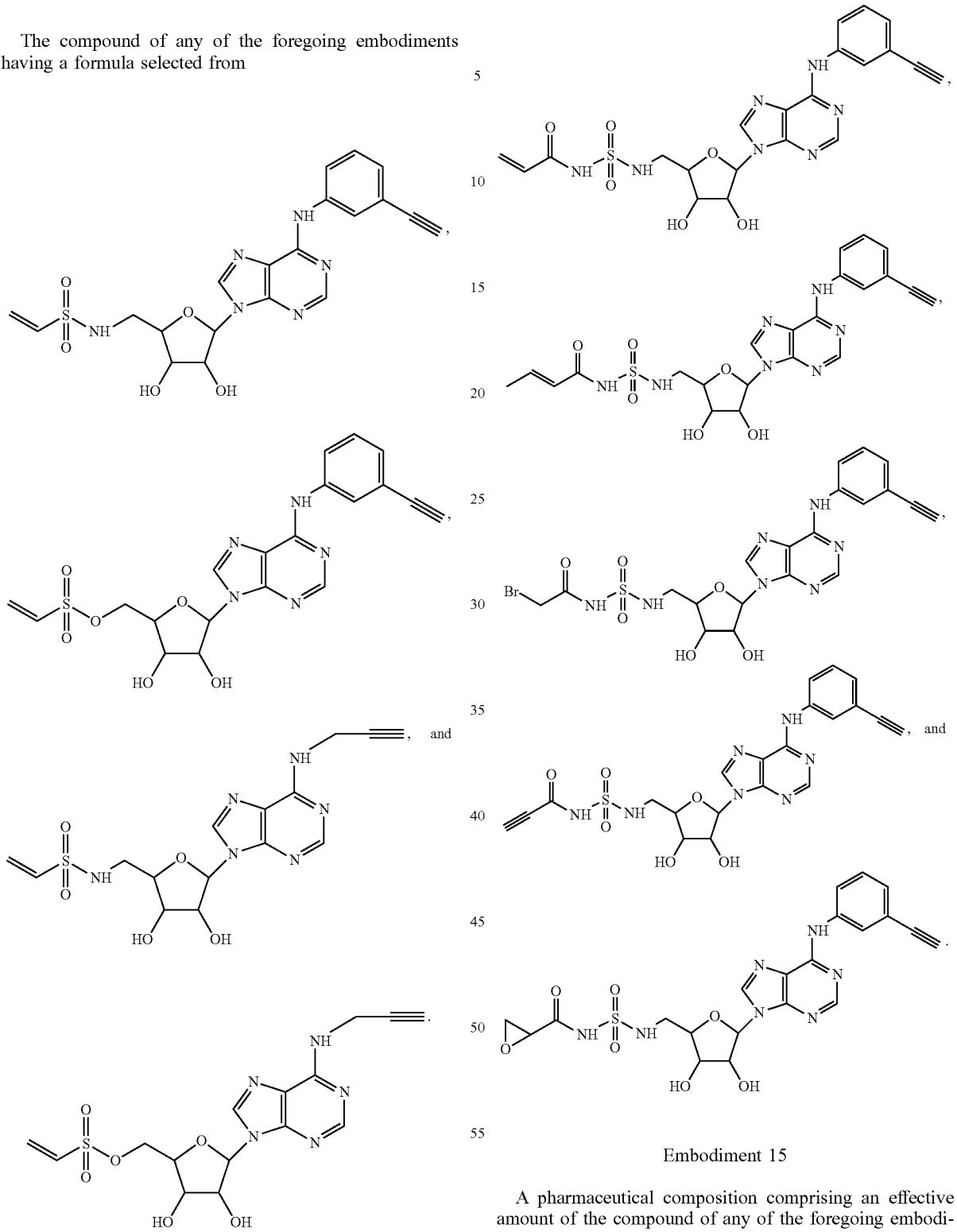

Embodiment 14

The compound of any of the foregoing embodiments having a formula selected from:

Embodiment 15

A pharmaceutical composition comprising an effective amount of the compound of any of the foregoing embodiments together with a carrier, excipient, or diluent.

Embodiment 16

A method of treating a subject in need thereof, the method comprising administering the compound of any of embodiments 1-14 or the pharmaceutical composition of embodiment 15 to the subject.

Embodiment 17

The method of embodiment 16, wherein the subject has a disease or disorder that is treated by inhibiting ubiquitin-like modifier-activating enzyme ATG7, optionally wherein the disease or disorder is selected lung cancer (e.g., non-small cell lung cancer and/or K-Ras driven lung cancer), melanoma (e.g., V600E B-Raf melanoma), pancreatic cancer (e.g., K-Ras driven pancreatic cancers), colon cancer, cancer of the central nervous system, ovarian cancer, renal cancer, prostate cancer, breast cancer, multiple myeloma, leukemia, and any other cancer whose proliferation depends on autophagy.

EXAMPLES

The following Example is illustrative and is not intended to limit the scope of the claimed subject matter.

Reference is made to the dissertation entitled "Investigating Ubiquitin-like Protein Activating Enzymes Using Chemical Approaches," by doctoral candidate Heeseon An, Department of Chemistry, Northwestern University, December 2015, the content of which is incorporated herein by reference in its entirety. Reference is made in particular to Chapter 3 entitled "New Strategy to Develop Selective Inhibitors of Autophagy."

Introduction

Macroautophagy (hereafter autophagy) is a cellular degradation process that digests long-lived proteins and organelles, complementing the ubiquitin proteasome system.[1] The autophagic process protects cells from stresses by removing dysfunctional or damaged organelles. Accordingly, autophagy is stimulated during various cellular stress conditions, such as nutrient starvation, oxidative stress, unfolded protein response, and infections. Autophagy exerts various functions in human diseases. In cancers, autophagy plays dual roles: suppressing tumorigenesis and promoting the growth of existing tumor. A recent study showed that autophagy functions as a tumor suppressor by inducing cell senescence through autophagy-dependent nuclear lamina degradation.[2] In the established tumors, however, autophagy assists the progression of the cancer cells by reducing inherent metabolic stresses. More specifically, autophagy limits the generation of reactive oxygen species in cancers and provides ample amount of nutrients via degradation of unnecessary organelles. Given the divergent role of autophagy in cancers, it is critical to dissect the autophagy in various cancer types, stages, and microenvironments for evaluating autophagy as a new therapeutic target to treat cancers.

Small molecule modulators of autophagy will serve as powerful tools for reversible and temporal control of autophagy, complementing the permanent genetic intervention methods. In addition, modulating the functions of autophagy-related proteins with small molecular probes would have greater relevance to drug development than genetic alteration methods. Therefore, development of small molecule activators and inhibitors are urgently needed to deconvolute the complicating roles of autophagy in cancers. Currently, there are two types of small molecule inhibitors of autophagy broadly used for basic research: 1) inhibitors of lysosomal functions and 2) inhibitors of PI3K family. However, the current pharmacological targets, i.e. lysosome and PI3K, regulate various cellular processes in addition to autophagy. Thus, plethoric effects of such inhibitors complicate data analysis. For example, preclinical studies have shown that a lysosomal degradation inhibitor, hydrochloroquin, exerts additive effects on killing cancers when co-treated with other cancer treatments. Although available data suggest that hydrochloroquin inhibits autophagy as evidenced by the decrease in the level of LC3-II, a possibility cannot be ruled out that the additive cytotoxicity is contributed by the inhibition of lysosomal functions that are not related with autophagy. Another limit of the currently used autophagy inhibitors is exemplified by the complex role of 3-methyladenine, a non-specific inhibitor of PI3K family. While 3-methyladenine temporarily blocks class III PI3K and inhibits autophagy, it also inhibits class I PI3K, which results in the activation of autophagy. The non-specificity of 3-methyladenine induces complicating results depending on the different cell context.[3] Collectively, the limits of current autophagy inhibitors underscore the urgent need to find novel protein targets for specific down-regulation of autophagy. Subsequently, designing small molecules that can selectively modulate such protein targets will facilitate the development of selective inhibitors of autophagy.

Here we hypothesize that ATG7 should be an ideal target of pharmacologic perturbation of autophagy because of the exclusive role of ATG7 in autophagy. Indeed, deletion of the ATG7 gene caused tumor growth arrest in mice models of lung tumors and pancreatic tumors, further supporting the therapeutic potential of ATG7 inhibitors[4-6] ATG7 is a UBL activating E1 enzyme that activates the C-terminus of two UBL proteins, ATG12 and ATG8 family. The conjugation of ATG8 to phosphatidyl ethanolamine is critical for autophagosomal membrane formation. Therefore, inhibition of ATG7 would block the entire autophagic process by inhibiting the initial autophagosome formation. ATG7 is potentially druggable due to the presence of ATP binding site in the catalytic center. However, an available small molecule modulator of ATG7 is currently lacking. In this study, we began to address the pharmacological potential of ATG7 by developing small molecule inhibitors of ATG7.

Results and Discussion

Design Strategies to Develop Selective Inhibitors of ATG7.

To date, eight E1 enzymes have been discovered in humans, which are categorized into two groups: canonical E1s and non-canonical E1s. The overall mechanisms of enzymatic actions and macromolecular structures are conserved among all E1s (FIG. 1). However, canonical E1s are characterized by the use of two equivalents of ATP and UBL proteins for full enzymatic action. In addition, the catalytic cysteines of the canonical E1s, such as UBA1, UBA2, and UBA3, are located >30 Å away from the ATP binding centers, requiring large structural rearrangements for the nucleophilic attack on the acylphosphate of UBL-AMP intermediate to form E1-UBL thioester complex (FIG. 1A). In contrast, ATG7 is a non-canonical E1 and requires one equivalent ATP and ATG8 (UBL). Interestingly, its catalytic cysteine is positioned on a flexible loop near the ATP binding center. The distance between the catalytic cysteine and ATP binding center in ATG7 is ~7 Å, the closest among E1 enzymes (FIG. 1B). The crystal structure of another non-canonical E1, UBA5, shows a 17 Å distance, which is shorter than canonical E1s but longer than ATG7 (FIG. 1C).

Figure 2:
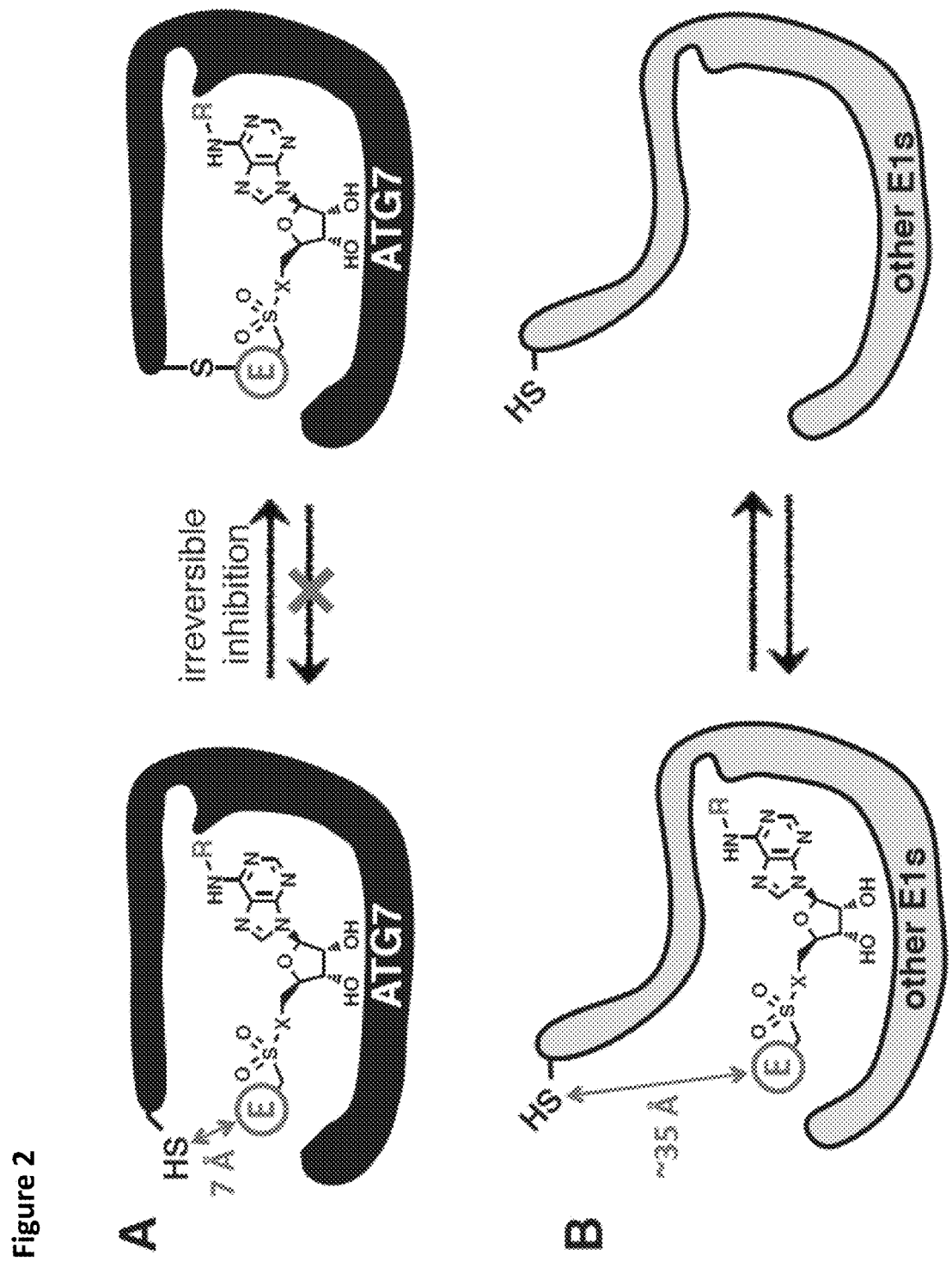
FIG. 2. Schematic description of the reaction between AMP-mimic electrophile and E1s (A) AMP-mimic electrophile binds to ATP binding center of ATG7, followed by the covalent labeling with catalytic cysteine (B) AMP mimic electrophile may bind to other E1s, yet the covalent labeling may not occur due to the long distance between the cysteine and electrophile.
Figure 3:
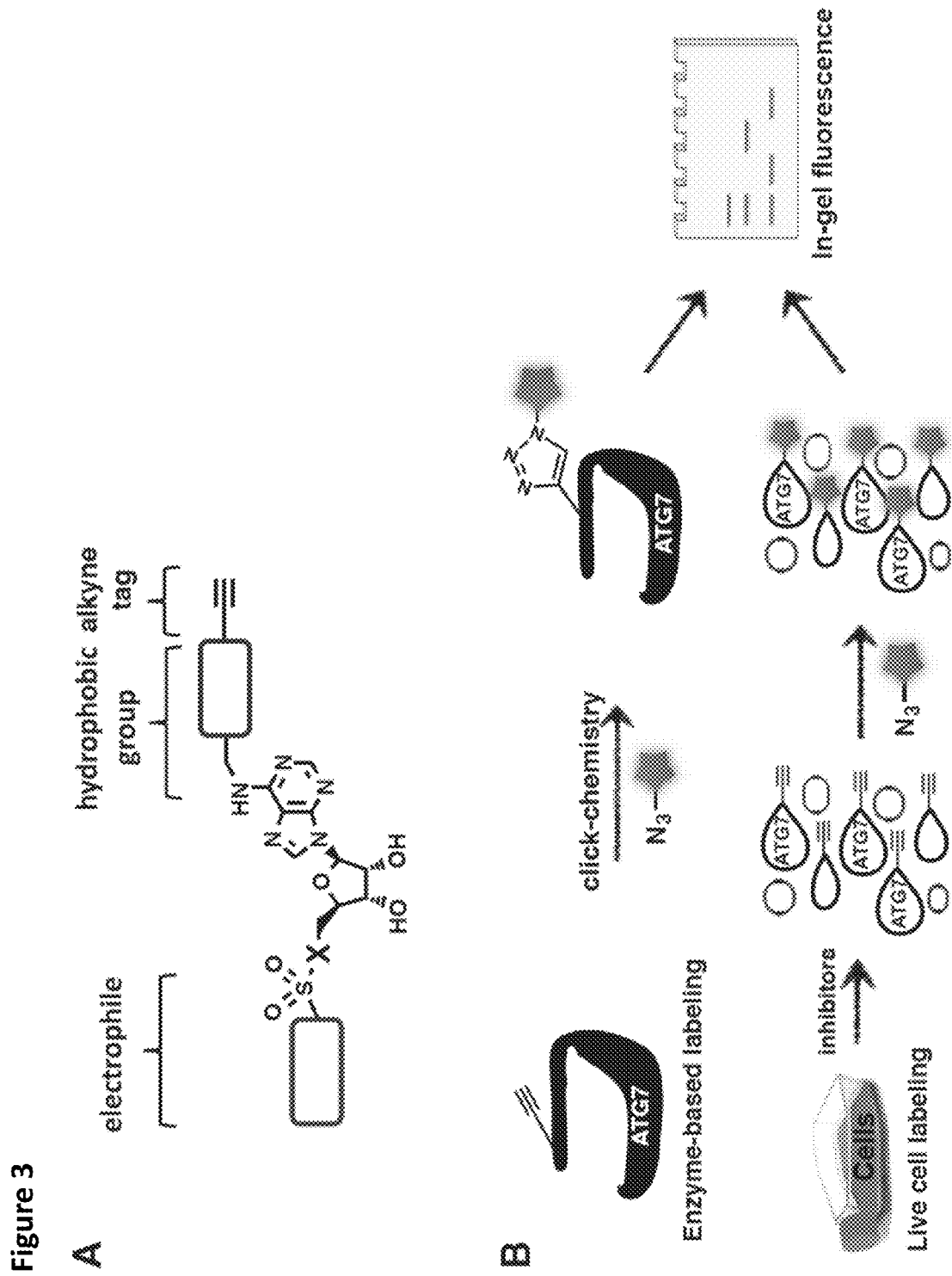
FIG. 3. Design strategy for electrophilic AMP analogs (A) Basic scaffold of the proposed AMP analogs (B) Schematic description of enzyme- and cell-based screening of AMP analogs using the click chemistry technique.
Figure 4:
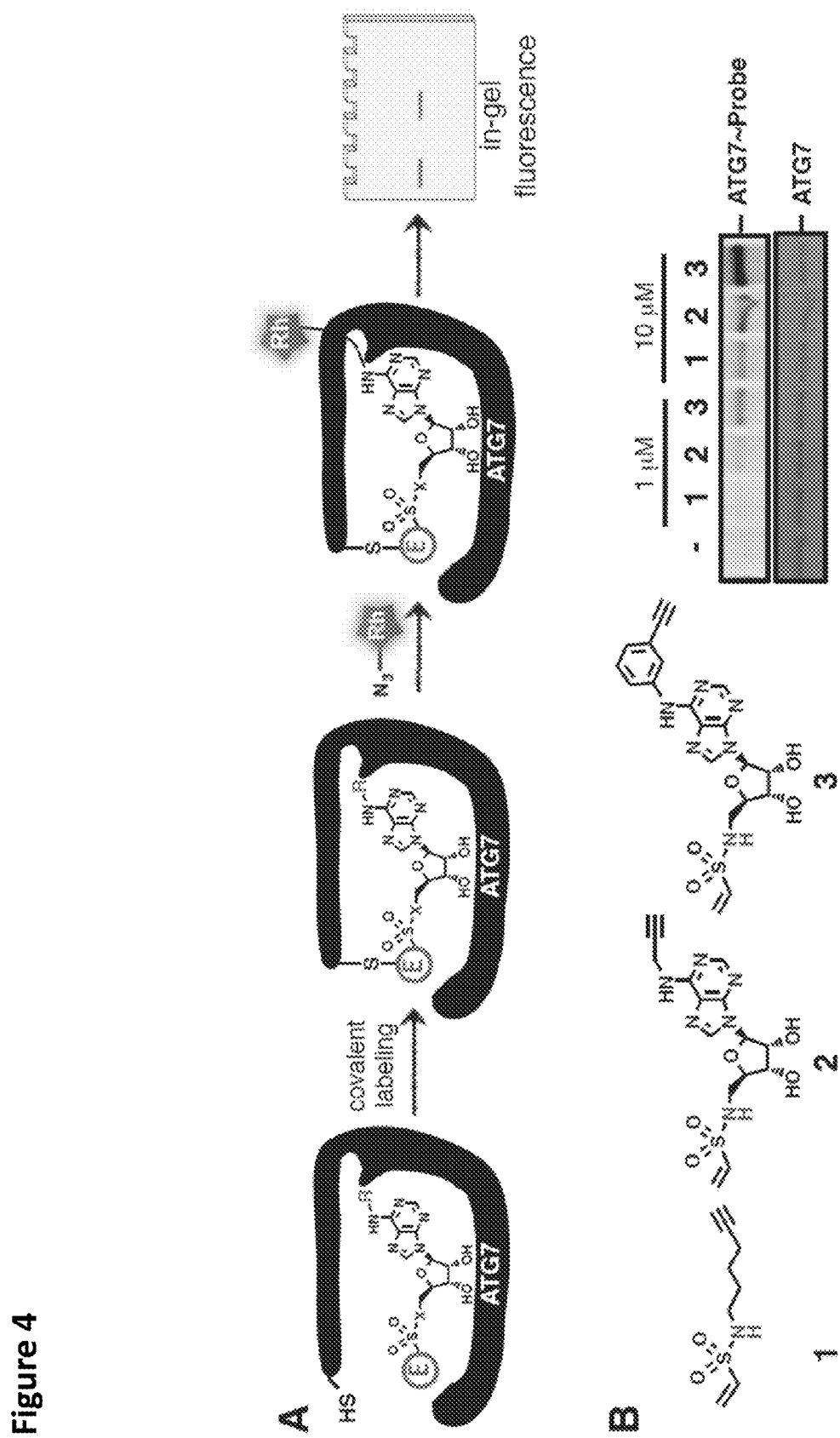
FIG. 4. Labeling of ATG7 with vinylsulfonamide-fused AMP analogs (A) Schematic description of the ATG7-labeling efficiency screening (B) Compound 3 most potently labels ATG7 in vitro.

Based on such difference of proximity between the ATP binding center and catalytic cysteine, we rationalized that electrophile containing AMP analogs at the 5'-OH position should be ideal to selectively target the catalytic cysteine of ATG7, when designed properly (FIG. 2). The AMP scaffold will direct the small molecules to the ATP binding center of ATG7. Then, the catalytic cysteine on the flexible loop will attack the electrophile given the close proximity, resulting in irreversible inhibition of ATG7. Since other E1s have their catalytic cysteines >30 Å away from their ATP binding site, those cysteines should be inefficient for labeling the electrophilic AMP analogs (FIG. 2B). When designing the electrophile-fused AMP analogs, we focused on the modulation of two elements to prepare selective and potent inhibitors: (1) the hydrophobic substituent at the N6-position of the adenine moiety and (2) the electrophile at the 5'-position (FIG. 3A). By modulating the substituent at the N6-position, which binds to the hydrophobic binding pocket of ATG7, we will control the binding affinity of the inhibitor candidates to ATG7. The N6-substituent would also reduce potential off-targets such as kinases or other adenosine-binding proteins by providing a steric clash with the proteins. By adding different types of electrophiles with different linker lengths, we will select the most potent electrophiles for nucleophilic attack. Finally, we added an alkyne group to the small molecules for the efficient screening of their selectivity and potency on ATG7 inhibition in vitro and in live cell.

Synthesis of Vinyl Sulfonamide Containing AMP Analogs.

To prove if the modulation of N6-position provides a selectivity filter via binding affinity changes, we initially prepared vinyl sulfonamide-fused AMP analogs (Scheme 1).

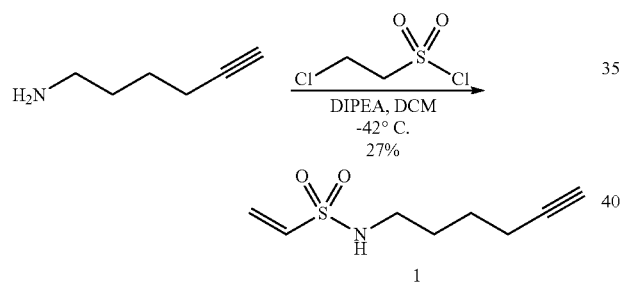

In order to test the importance of the AMP moiety as a directing group, we prepared a control molecule (1) that does not have an AMP moiety (Scheme 1). The treatment of 6-amino-1-hexyne with 2-chloroethanesulfonyl chloride resulted in desired product 1.

Next, electrophilic AMP analogs with two significantly different substituents at N6-position (i.e. a propargyl and phenyl alkyne) were synthesized following Scheme 2 and Scheme 3. Compound 2 that has a small hydrophobic group (propargyl alkyne) at the N6-position was prepared by coupling 2-chloroethanesulfonyl chloride with the 5'-amino adenine moiety, followed by the deprotection of the acid labile acetonide (Scheme 2). The synthesis of compound 3, which has a large hydrophobic group (phenyl alkyne) at the N6-position, required tert-butyldimethylsilane (TBDMS) protection and deprotection steps on the 5' alcohol and Boc protection on the N6-amine due to the instability of the reaction intermediates during the Mitsunobu reaction. Subsequent treatment with 2-chloroethanesulfonyl chloride and global deprotection of the acid labile protecting groups led to the formation of compound 3.

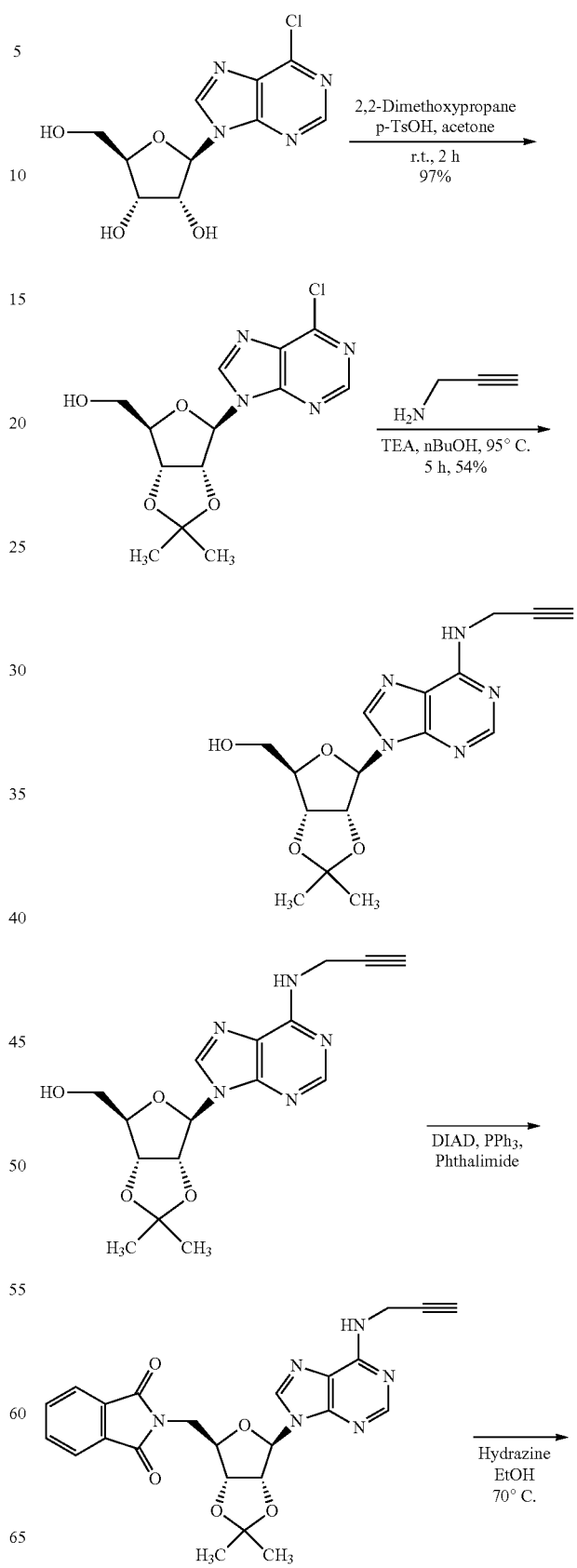

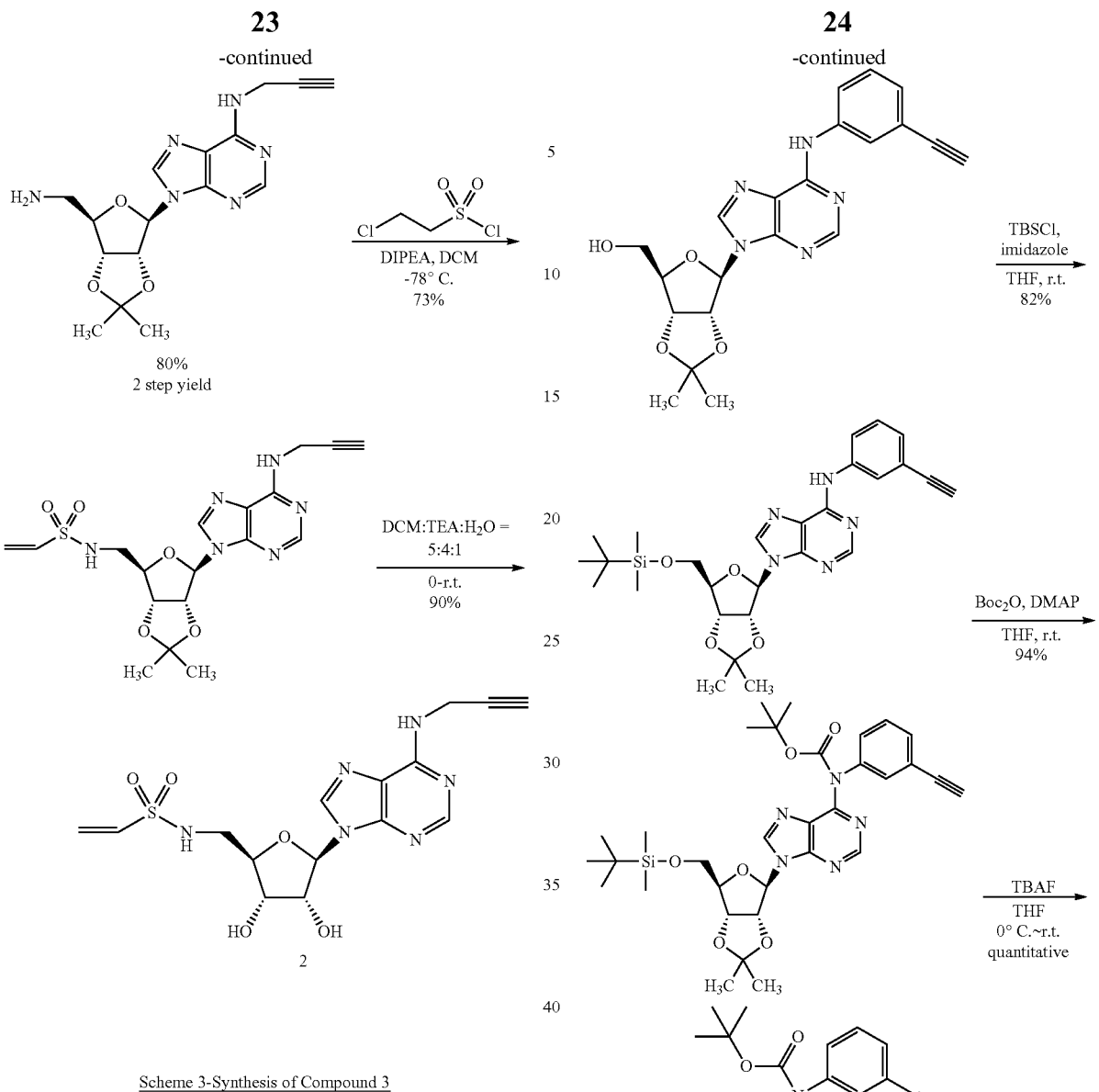
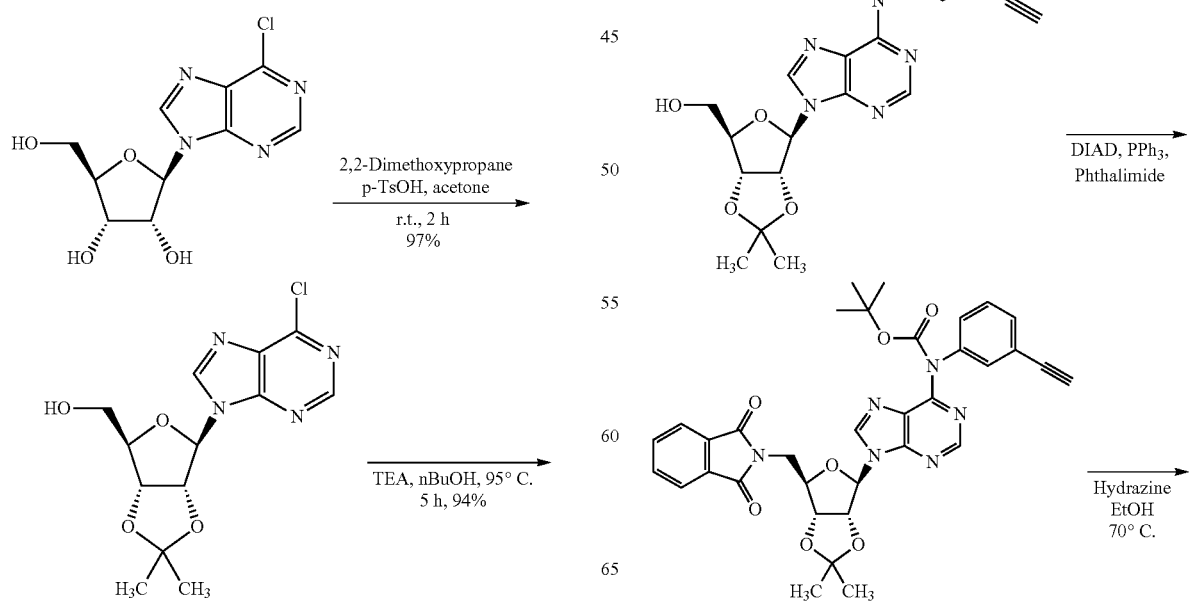
Scheme 3-Synthesis of Compound 3

-continued

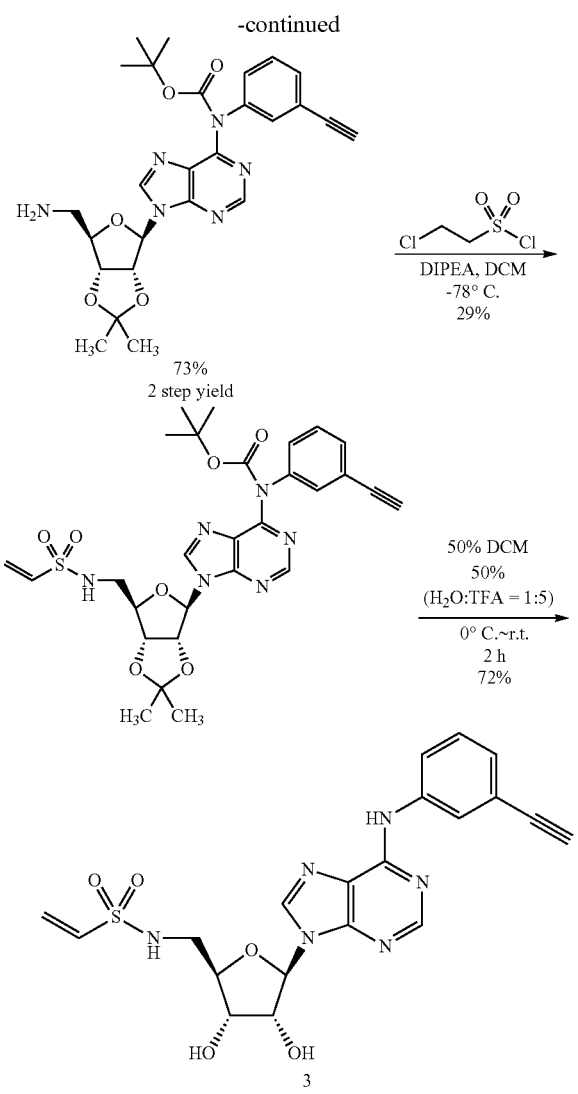

3 probes: vinyl sulfonate-fused AMP analogs having either propargyl or phenyl alkyne substituent (Scheme 4 and Scheme 5).

Scheme 4 - Synthesis of Compound 4

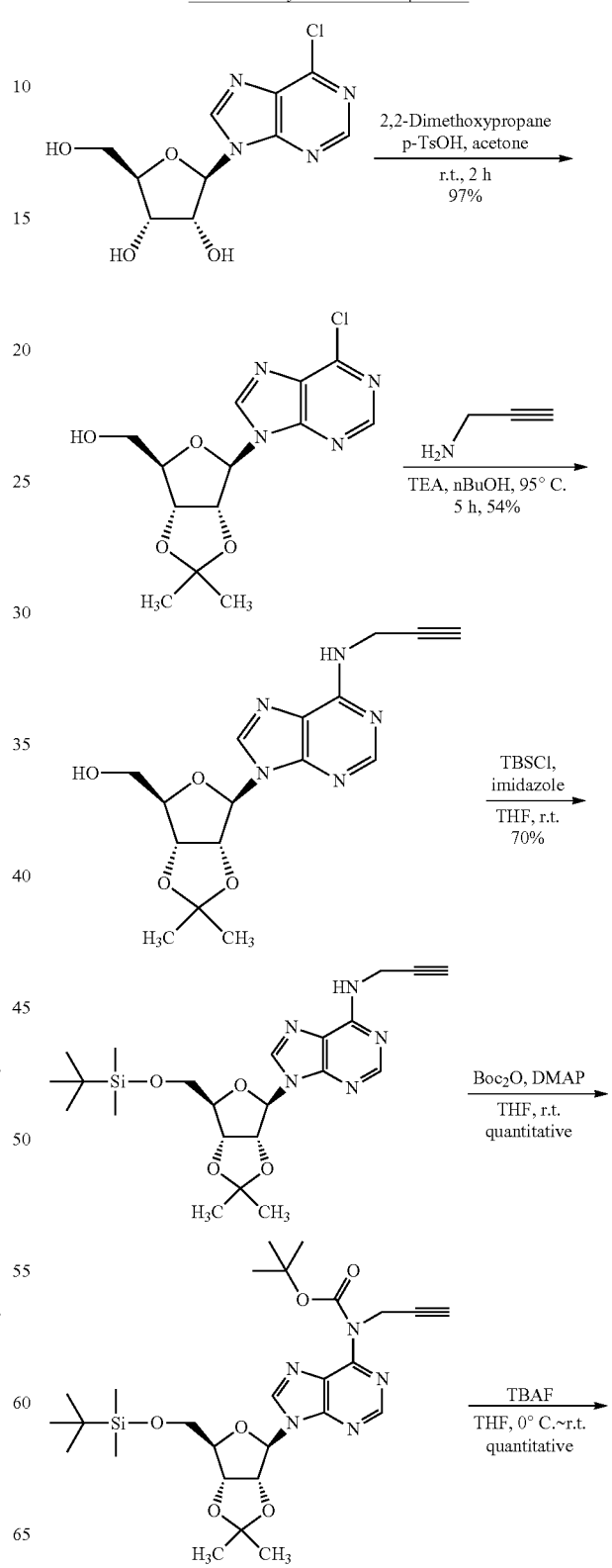

Labeling of ATG7 Using Vinyl Sulfonamide-Fused AMP Analogs In Vitro.

Following the synthesis, we incubated probes 1, 2, and 3 with catalytically active ATG7 (0.5 μM) for 3 hours. Then the click chemistry was followed to measure the levels of small molecule labeled ATG7. The intensity of the fluorescent bands was interpreted as the labeling efficiency of the probes. As we expected, control molecule 1 showed little labeling at 10 μM concentration, suggesting that the AMP moiety plays critical functions as a directing group.

Interestingly, phenyl alkyne containing molecule 3 showed higher labeling efficiency than 2. Overall, our initial test suggested that the electrophilic AMP probes label ATG7 by binding to the ATP binding site. Also, the modulation of the N6-position with different hydrophobic groups provides different labeling efficiency to ATG7, as evidenced by the phenyl-N6 substituent being more efficient than the propargyl group.

Synthesis of Vinyl Sulfonate—Fused AMP Analogs and their ATG7 Labeling Efficiency.

To further confirm the results that 1) electrophilic AMP labels ATG7 using the ATP binding center and 2) phenyl alkyne on the N6-position is more potent in labeling ATG7 than the propargyl alkyne, we synthesized a different set of

27
-continued
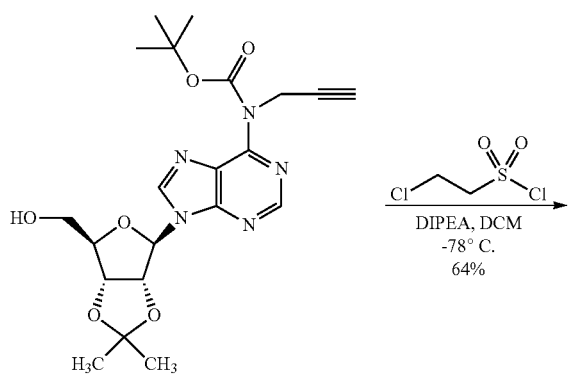
28
-continued
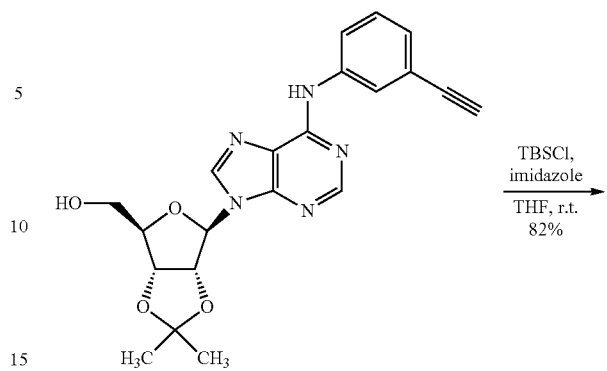
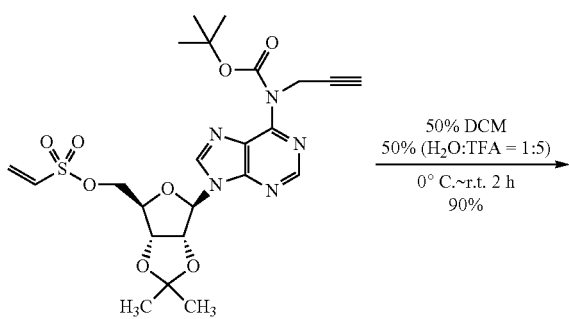
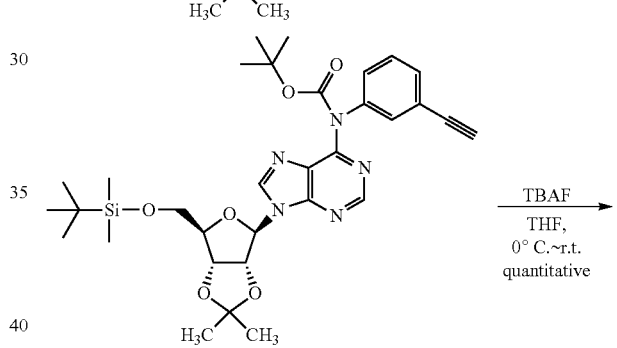
Scheme 5 - Synthesis of Compound 5
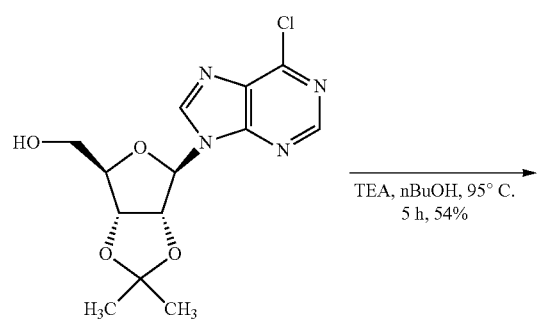
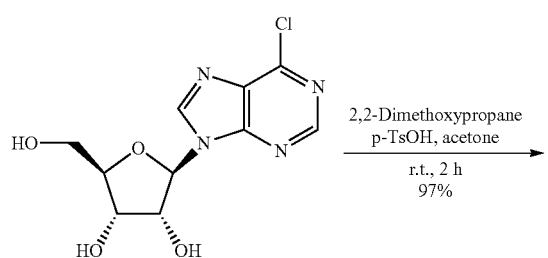
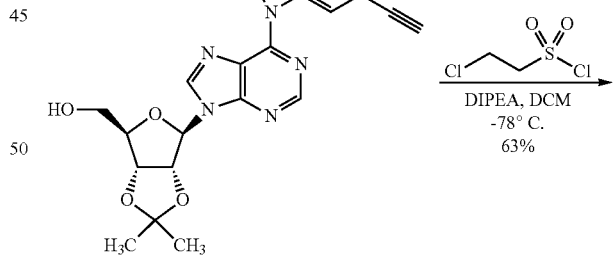
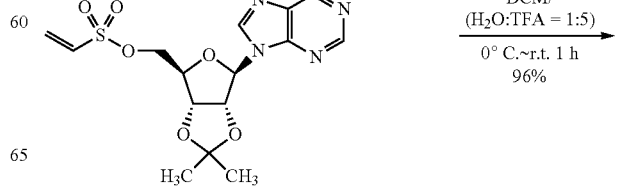

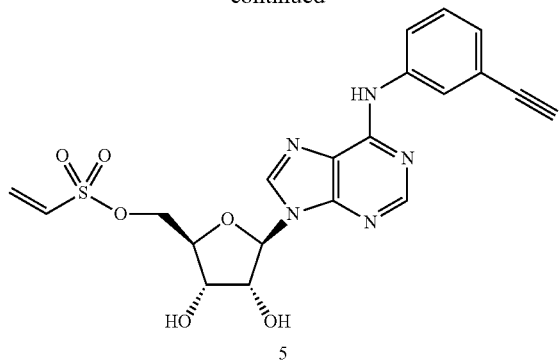

5

Figure 5:
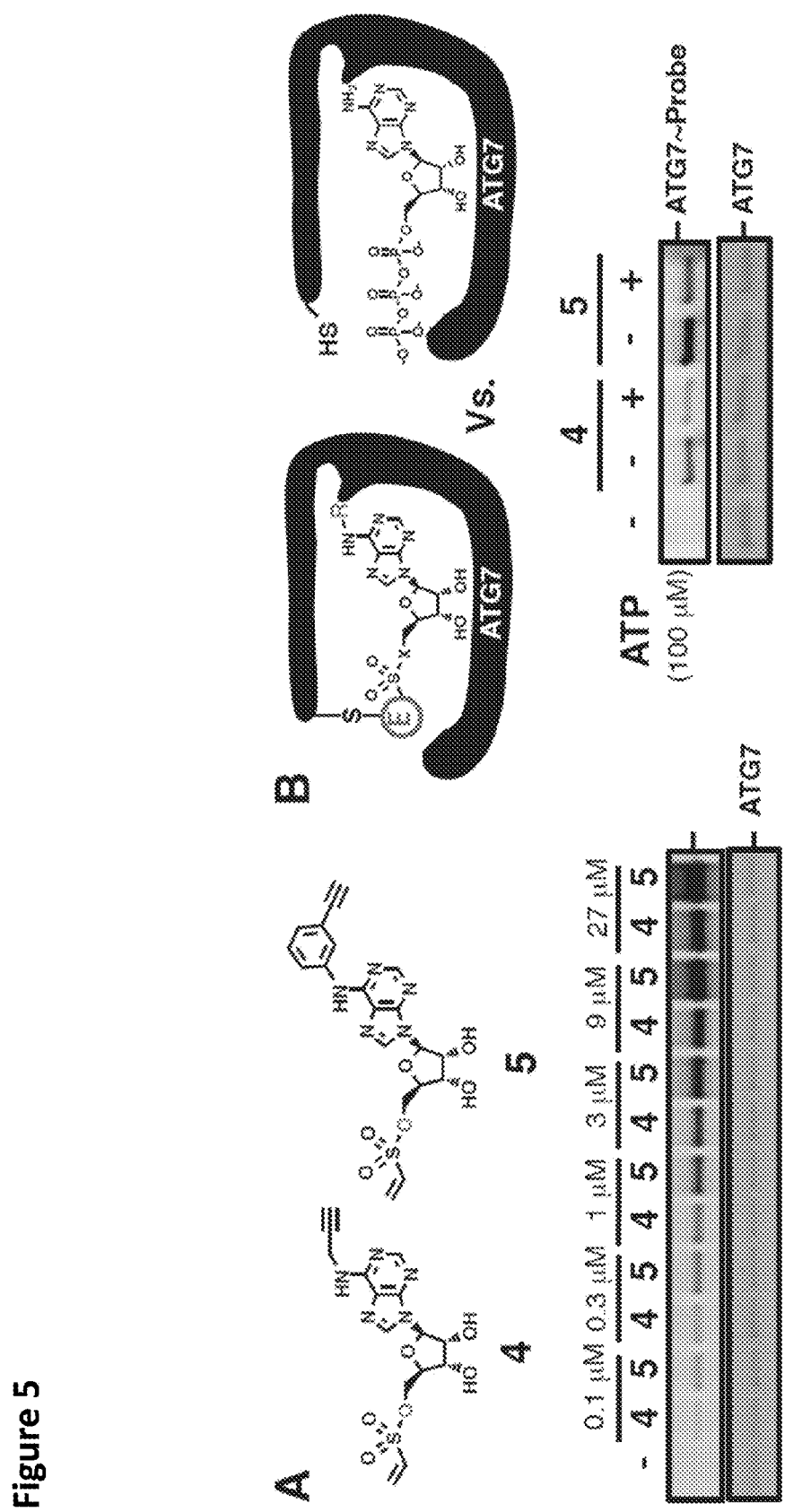
FIG. 5. Labeling of ATG7 with vinyl sulfonate-fused AMP analogs (A) compound 5 showed greater labeling potency than compound 4 (B) ATP competition reaction result suggests that compound 4 and 5 utilize ATP binding site for the ATG7 labeling.

Subsequently, increasing concentrations of compounds 4 and 5 were incubated with catalytically active ATG7 (0.5 μM) for 3 hours. The following conjugation of rhodamine azide via click chemistry and in-gel fluorescent scanning showed the compounds-labeled ATG7 bands in SDS-PAGE. As we expected, compound 5-treated ATG7 showed a stronger intensity of the fluorescent bands than compound 4-treated ATG7, confirming that large hydrophobic substituents at the N6-position do induce higher affinity and more efficient labeling of ATG7 (FIG. 5A). We also conducted an ATP-competition reaction to test if compounds 4 and 5 utilize the ATP binding site for the covalent labeling. ATG7 was incubated with compound 4 or 5 in the presence or absence of ATP (100 μM) (FIG. 5B). The subsequent click-chemistry and in-gel fluorescent scanning revealed that when there presents a large quantity of ATP, the labeling of ATG7 by compounds 4 and 5 significantly dropped compared to the ATP free conditions. Together with the inefficient labeling of ATG7 by compound 1, an ATP competition reaction strongly suggests that the binding to the ATP binding site is critical for the electrophile-fused AMP mimic molecules to label ATG7.

Labeling of Proteins by Electrophilic AMP Probes in Live A549 Cells.

Figure 6:
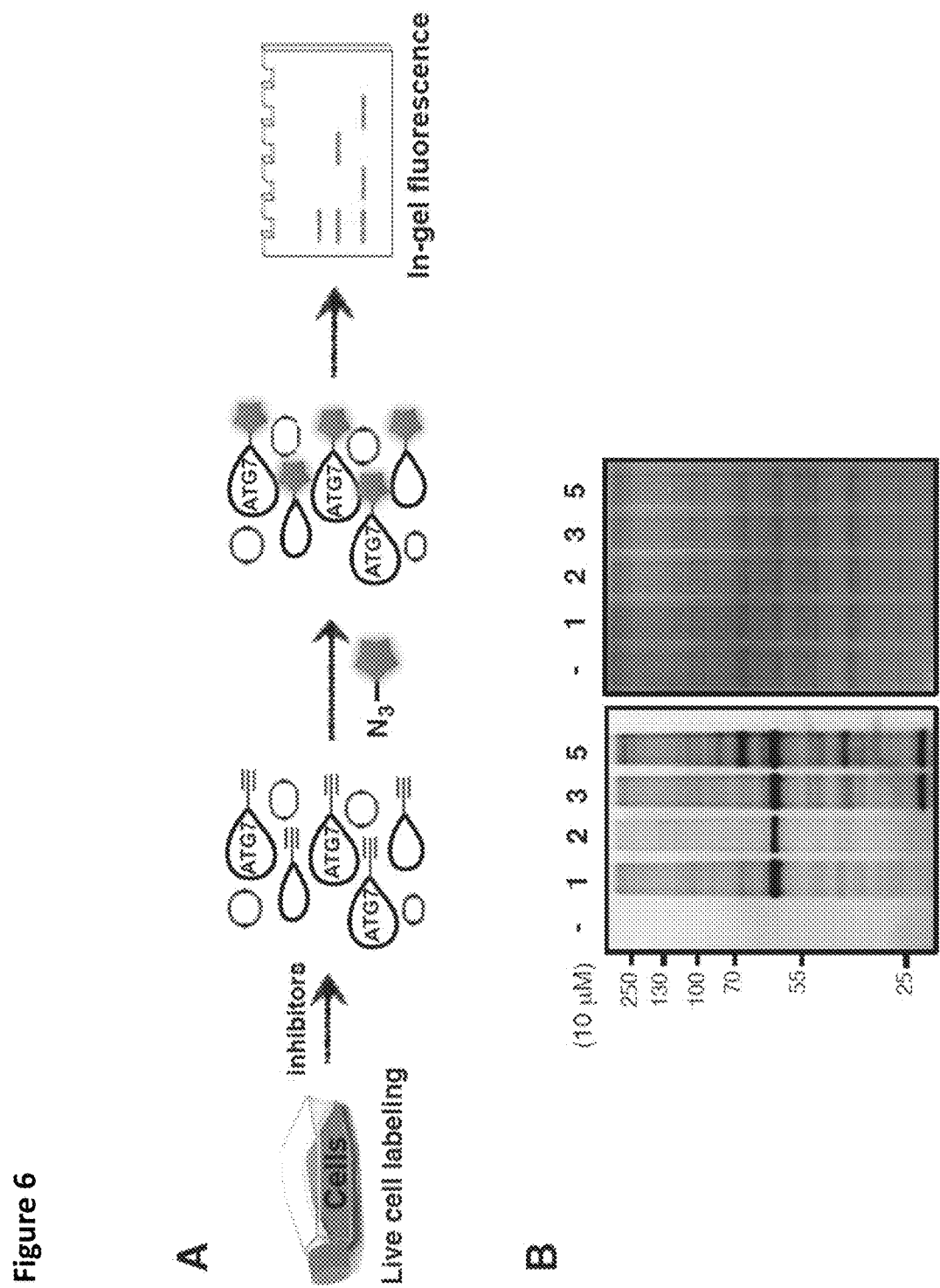
FIG. 6. Labeling of proteins with AMP analogs in live A549 cells (A) Schematic description of the live cell based labeling experiment (B) In-gel fluorescence image of the A549 lysates after treated with probes; 1, 2, 3, and 5.
Figure 7:
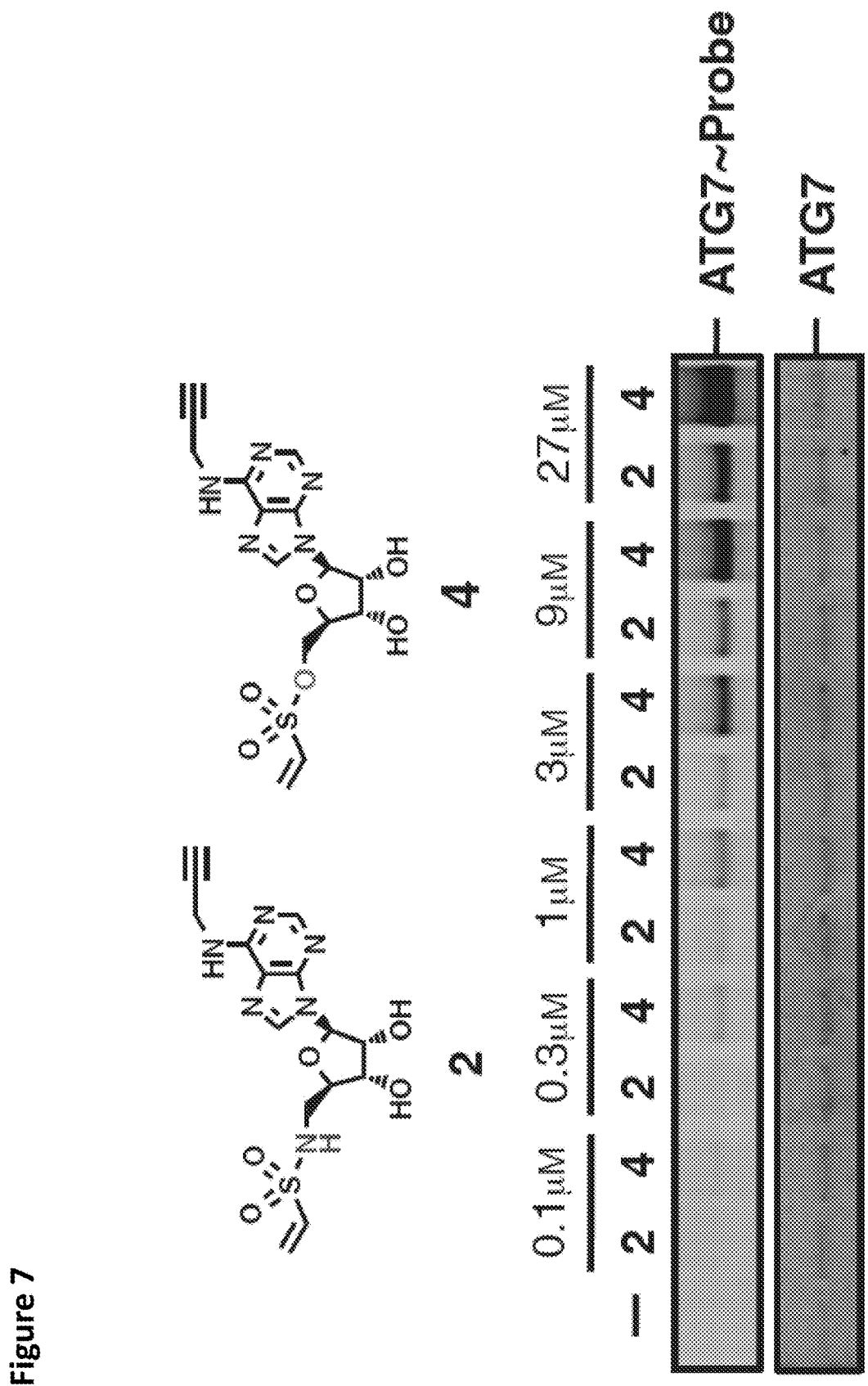
FIG. 7. Labeling efficiency comparison between vinyl sulfonamide and vinyl sulfonate.

We investigated the labeling of proteins with the developed probes inside of live cells. To this end, A549 cells were treated with 10 μM of compounds 1, 2, 3, and 5 for 2 hours. Then, the lysate was treated with click reaction mixtures containing rhodamine azide. Subsequent in-gel fluorescence scanning showed multiple fluorescent bands, indicating that the probes are cell permeable and able to label proteins in live cells (FIG. 6). The result also suggests that the vinyl sulfonamide and vinyl sulfonate react with other proteins. These non-specifically labeled proteins do not necessarily have an adenosine binding site, given the labeling of proteins by compound 1 (FIG. 6). Furthermore, vinyl sulfonate containing compound 5 showed more numbers of off-targets when compared with compound 3. This is in agreement with our enzyme based labeling test, in which vinyl sulfonate showed greater labeling efficiency of ATG7 than vinyl sulfonamide, possibly due to the high innate chemical reactivity (FIG. 7). Overall results suggest that vinyl sulfonate and vinyl sulfonamides are reactive electrophiles that could induce non-specific labeling of surface cysteines present in A549 cell proteome.

CONCLUSION

In this study, we investigated a new approach to develop a selective inhibitor of autophagy. Given the exclusive function of ATG7 in autophagy, we hypothesized that pharmacologically targeting ATG7 will specifically inhibit autophagy with little effect on other cellular signaling pathways, in contrast to the currently used autophagy inhibitors.

To design a selective inhibitor of ATG7, we introduced new design strategies that include 1) targeting the ATP binding site of ATG7 via an AMP like scaffold, 2) labeling the catalytic cysteine with the electrophile fused at the 5'—OH group of the AMP moiety, and 3) having an alkyne tag as a detection handle for the live cell based drug screening system.

We prepared two sets of electrophile-fused AMP analogs: 5'-vinyl sulfonamide-fused AMP and 5'-vinyl sulfonate-fused AMP. Both of them contain either phenyl alkyne substituent or propargyl alkyne substituent at the N6-position of the adenine moiety. The developed compounds 1, 2, 3, 4, and 5 were tested for the efficiency of ATG7 labeling using click-chemistry based detection method. Interestingly, phenyl alkyne containing probes (3 and 5) showed much higher labeling efficiency than propargyl alkyne containing probes (2 and 4), regardless of the electrophiles. This result supports our hypothesis that modification of the N6-substituent will enable the discovery of small molecules that bind tightly to the ATP binding pocket of ATG7. Furthermore, we demonstrated that the adenine moiety is critical for the ATG7 labeling based on the inefficient labeling of ATG7 using control molecule 1.

The cell permeability of the probes was confirmed by live A549 cell based assays. Although the overall results indicate that the electrophile-fused AMP analogs can penetrate the cell membrane, a large quantity of non-specific proteins in live A549 cell was labeled by the five probes as well. This implies that the vinyl sulfamate and vinyl sulfonate are too reactive in nature, thus randomly reacting with surface cysteines to produce covalent adducts. Particularly, Probe 5, which bears a reactive vinyl sulfonate group, showed the strongest off target effects. These off-target effects suggest that suppressing the electrophilicity of the probes is required. We suggest that coupling various electrophiles at the sulfamide amine of the precursor compound as appeared in FIG. 3 may reduce the off-target effect based on the decreased electrophilicity of the β-substituted Michael acceptors. In addition, such molecules should have ~2.5 Å shorter distance toward the catalytic cysteine, thus providing greater chances of reacting with the catalytic cysteine of ATG7 and subsequent higher selectivity.

Bio-Experimental Protocols

General Information. Human recombinant ATG7 protein was purchased from R&D Systems and used without further purification. In-gel fluorescence imaging was performed on a Typhoon 9600 (GE Healthcare).

Labeling of ATG7 with probes 1, 2, 3, 4, and 5 in vitro. ATG7 (0.4 μM) and TCEP (100 μM) in buffer containing HEPES (25 mM, pH 7.6), NaCl (50 mM), and MgCl2 (4 mM) were treated with increasing concentrations of each probe at room temperature (10 μL total volume) for 2 h. The reaction mixtures were treated with 1 μl of 10% SDS followed by 4 μL of click reaction mixture: CuSO4 (final conc. 1 mM), TBTA (final conc. 100 μM), sodium ascorbate (final conc. 1 mM), and Azide-Fluor-585 (final conc. 100 μM). The reaction mixture was incubated for 30 min at r.t., followed by the addition of 3 μL of 6× Laemmli loading buffer, and resolved by 12% SDS-PAGE. The bottom of the gel was cut to eliminate the excessive amount of Azide-Fluor-585. The acrylamide gel was kept in 50% ddH2O, 40% EtOH and 10% Acetic acid solution until it was subjected to the in-gel scanning fluorescence imaging (Typhoon 9600, GE Healthcare). The proteins in the gel were then visualized with Instant Blue™.

In-Gel Fluorescent Detection of Probes 1, 2, 3, and 5 Labeled Proteomes in Live A549 Cells.

A549 cells were grown in RPMI medium (Life Technologies) supplemented with 10% fetal bovine serum in 6-well plates. Confluent A549 cells (9.6 cm$^2$ per condition in 6-well plates) were washed with Dulbecco's Phosphate-Buffered Saline (DPBS, 3 mL) and the growth medium was replaced with RPMI medium containing each probe. After 2 h incubation time at 37° C., cells were washed with DPBS (3 mL). 160 µL of lysis buffer containing Tris HCl (25 mM, pH 7.6), NaCl (150 mM), 1% NP40, 1% sodium deoxycholate, 0.1% SDS, and protease inhibitor cocktail for mammalian cells (Sigma-Aldrich, 1:100 v/v) was added to each well of the 6-well plates, and cells were lysed on ice for 10 min. The gathered lysate was flown through 21G syringe for the complete breakdown. The complete lysis of the cells was monitored using Carl Zeiss Primo Vert inverted microscope. 10 µL of each cell lysate was treated with sodium dodecyl sulfate (final concentration 1%), followed by the incubation with the click chemistry reagents (CuSO$_4$ (final conc. 1 mM), TBTA (final conc. 100 µM), sodium ascorbate (final conc. 1 mM) and Azide-Fluor-585 (final conc. 100 µM) for 30 min. Proteins were resolved by 10% SDS-PAGE, and subjected to in-gel scanning fluorescence imaging to visualize the covalent adducts. Total proteins in the gel were then visualized by staining the gel with Instant Blue™.

REFERENCES

1. Mizushima, N.; Komatsu, M. Cell 2011, 147, 728.
2. Dou, Z.; Xu, C.; Donahue, G.; Shimi, T.; Pan, J. A.; Zhu, J.; Ivanov, A.; Capell, B. C.; Drake, A. M.; Shah, P. P.; Catanzaro, J. M.; Daniel Ricketts, M.; Lamark, T.; Adam, S. A.; Marmorstein, R; Zong, W. X.; Johansen, T.; Goldman, R D.; Adams, P. D.; Berger, S. L. Nature 2015, 527, 105.
3. Wu, Y. T.; Tan, H. L.; Shui, G.; Bauvy, C.; Huang, Q.; Wenk, M. R; Ong, C. N.; Codogno, P.; Shen, H. M. The Journal of biological chemistry 2010, 285, 10850.
4. Guo, J. Y.; Karsli-Uzunbas, G.; Mathew, R.; Aisner, S. C.; Kamphorst, J. J.; Strohecker, A. M.; Chen, G.; Price, S.; Lu, W.; Teng, X.; Snyder, E.; Santanam, U.; Dipaola, R. S.; Jacks, T.; Rabinowitz, J. D.; White, E. Genes & development 2013, 27, 1447.
5. Rosenfeldt, M. T.; O'Prey, J.; Morton, J. P.; Nixon, C.; MacKay, G.; Mrowinska, A.; Au, A.; Rai, T. S.; Zheng, L.; Ridgway, R.; Adams, P. D.; Anderson, K. I.; Gottlieb, E.; Sansom, O. J.; Ryan, K. M. Nature 2013, 504, 296.
6. Karsli-Uzunbas, G.; Guo, J. Y.; Price, S.; Teng, X.; Laddha, S. V.; Khor, S.; Kalaany, N. Y.; Jacks, T.; Chan, C. S.; Rabinowitz, J. D.; White, E. Cancer discovery 2014, 4, 914.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound of Formula Ib':

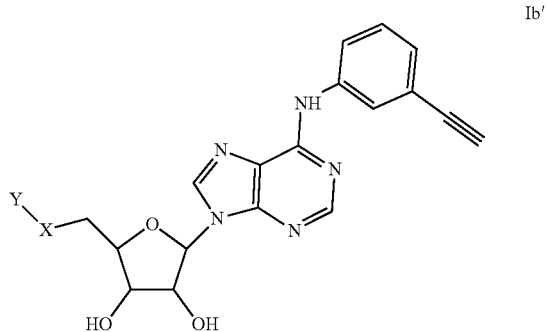

wherein:
X is CH$_2$, NH, O, or S;
Y is an electrophile;
or Y and X together form a 3-membered, 4-membered, 5-membered, 6-membered, or 7-membered carbocycle or heterocycle which optionally is unsaturated at one or more bonds and which optionally includes a carbonyl substituent.

2. The compound of claim 1, wherein Y is selected from the group consisting of:

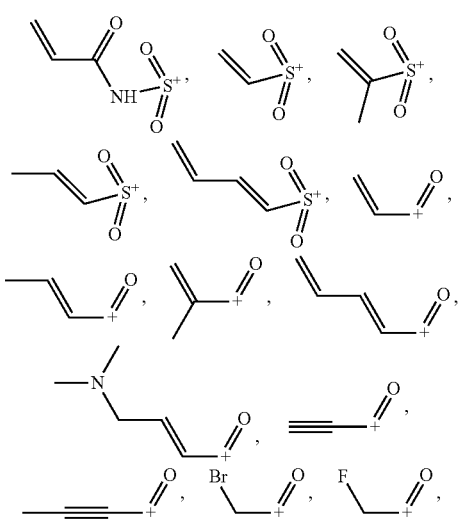

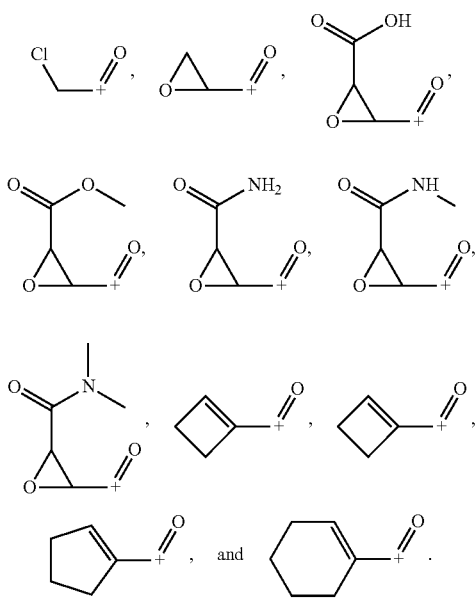

3. The compound of claim 1, wherein Y and X form a 3-membered, 4-membered, 5-membered, 6-membered, or 7-membered homocycle or heterocycle which optionally is unsaturated at one or more bonds and which optionally includes a carbonyl substituent.

4. The compound of claim 3, wherein Y and X form an unsaturated heterocycle selected from

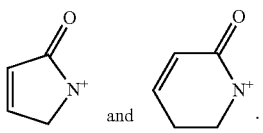 [SMILES: O=C1C=CC[NH2+]1 ; O=C1C=CCC[NH2+]1]

5. The compound of claim 1, wherein X is O or S.

6. The compound of claim 1, wherein X is NH.

7. The compound of claim 1, wherein X is CH$_2$.

8. The compound of claim 1, wherein the electrophile comprises a vinyl group.

9. The compound of claim 1 having a formula selected from

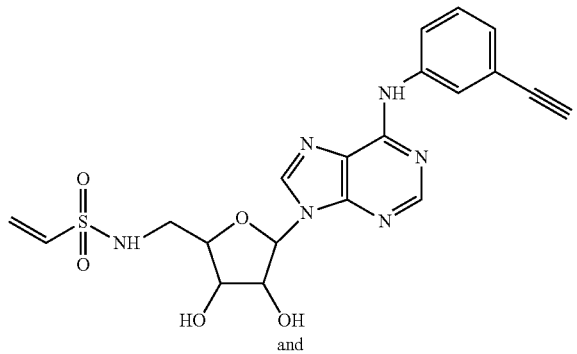

and

10. The compound of claim 1 having a formula selected from:

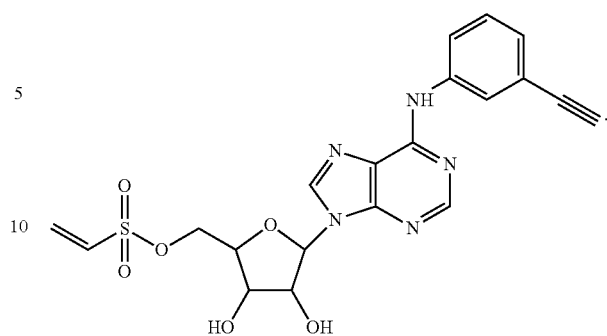

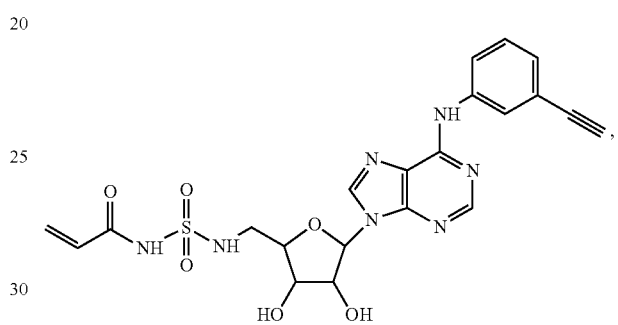

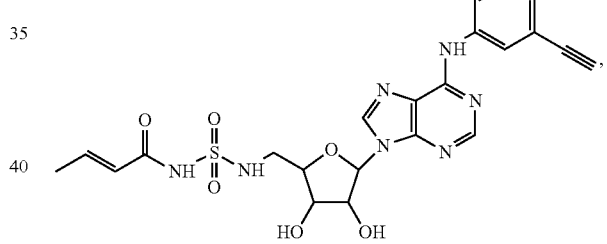

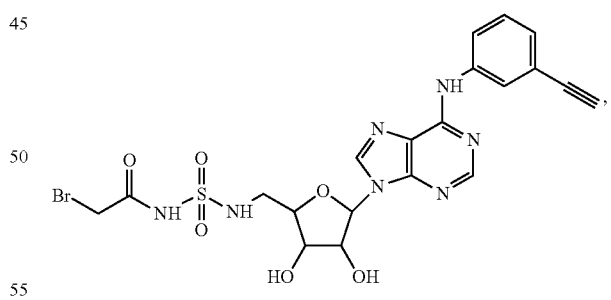

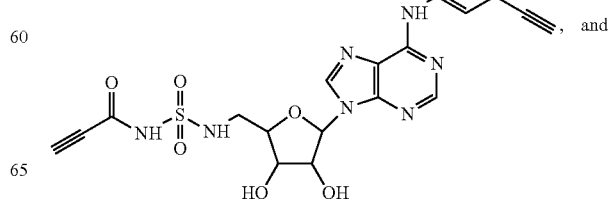

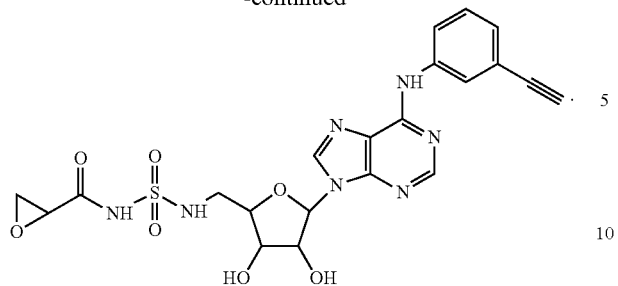

11. A pharmaceutical composition comprising an effective amount of the compound of claim 1 together with a carrier, excipient, or diluent.

12. A method of treating a subject having a disease or disorder characterized by ubiquitin-like modifier-activating enzyme ATG7 activity, the method comprising administering the pharmaceutical composition of claim 11 to the subject.

13. The method of claim 12, wherein the subject has cancer.

14. The method of claim 13, wherein the cancer is selected from lung cancer, melanoma, pancreatic cancer, colon cancer, cancer of the central nervous system, ovarian cancer, renal cancer, prostate cancer, breast cancer, multiple myeloma, and leukemia.

* * * * *